United States Patent
Santori et al.

(10) Patent No.: US 10,240,978 B2
(45) Date of Patent: Mar. 26, 2019

(54) OPTICAL SPECTROMETER

(71) Applicant: Hewlett-Packard Development Company, L.P., Houston, TX (US)

(72) Inventors: Charles M. Santori, Palo Alto, CA (US); Alexander Govyadinov, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 15/546,917

(22) PCT Filed: Apr. 30, 2015

(86) PCT No.: PCT/US2015/028639
§ 371 (c)(1),
(2) Date: Jul. 27, 2017

(87) PCT Pub. No.: WO2016/175859
PCT Pub. Date: Nov. 3, 2016

(65) Prior Publication Data
US 2018/0045562 A1    Feb. 15, 2018

(51) Int. Cl.
*G01N 21/25*    (2006.01)
*G01J 3/02*    (2006.01)
*G01N 21/64*    (2006.01)
*B01L 3/00*    (2006.01)
*G01N 15/14*    (2006.01)
*G01N 21/05*    (2006.01)

(52) U.S. Cl.
CPC ........ *G01J 3/0218* (2013.01); *B01L 3/50273* (2013.01); *B01L 3/502715* (2013.01); *G01J 3/0259* (2013.01); *G01N 15/1436* (2013.01); *G01N 15/1484* (2013.01); *G01N 21/648* (2013.01); *B01L 2300/0654* (2013.01); *B01L 2400/0442* (2013.01); *G01N 15/1459* (2013.01); *G01N 21/05* (2013.01); *G01N 2021/6482* (2013.01)

(58) Field of Classification Search
CPC ........ G01N 21/78; G01N 21/76; G01N 21/64; G01N 21/65; G01N 35/10; G01N 15/14; H01L 31/167; F21V 8/00; G01J 3/46; G01J 3/02
See application file for complete search history.

(56) References Cited

U.S. PATENT DOCUMENTS 8,561,456 B2   10/2013   Meredith et al.
8,926,906 B2    1/2015   Packirisamy et al.
(Continued)

FOREIGN PATENT DOCUMENTS

JP   S51-101190 U   2/1975
JP   H10-206316 A   8/1998
(Continued)

*Primary Examiner* — Abdullahi Nur
(74) *Attorney, Agent, or Firm* — Rathe Lindenbaum LLP

(57) ABSTRACT

Provided in one example is an apparatus, including a microfluidic channel supported by a substrate. An optical spectrometer includes a waveguide supported by the substrate. The waveguide includes a coupler and outcouplers. A light source directs light to the coupler of the waveguide. Optical sensors are supported by the substrate. Each of the optical sensors is optically coupled to one of the outcouplers.

15 Claims, 20 Drawing Sheets

(56) References Cited

U.S. PATENT DOCUMENTS

| | | |
|---|---|---|
| 2004/0026617 A1 | 2/2004 | Gregori et al. |
| 2005/0151966 A1* | 7/2005 | Packirisamy ......... B82Y 20/00 |
| | | 356/328 |
| 2007/0298514 A1 | 12/2007 | Correia et al. |
| 2008/0180188 A1 | 7/2008 | Beerling et al. |
| 2009/0097022 A1 | 4/2009 | Shen et al. |
| 2011/0272575 A1 | 11/2011 | Kim et al. |

FOREIGN PATENT DOCUMENTS

| | | |
|---|---|---|
| JP | 2001-141563 | 5/2001 |
| JP | 2005-270522 | 10/2005 |
| JP | 2006-064691 | 3/2006 |
| JP | 2013-083680 | 5/2013 |
| WO | PCT/US2012/034865 | 10/2013 |
| WO | WO-2014178827 | 11/2014 |

* cited by examiner

OPTICAL SPECTROMETER

BACKGROUND

Optical spectrometers detect the intensity of light as a function of wavelength or frequency. Existing spectrometers are difficult and expensive to fabricate. Existing spectrometers are not readily integrated into microfluidic systems for cytometry.

DETAILED DESCRIPTION OF EXAMPLES

Figure 1:
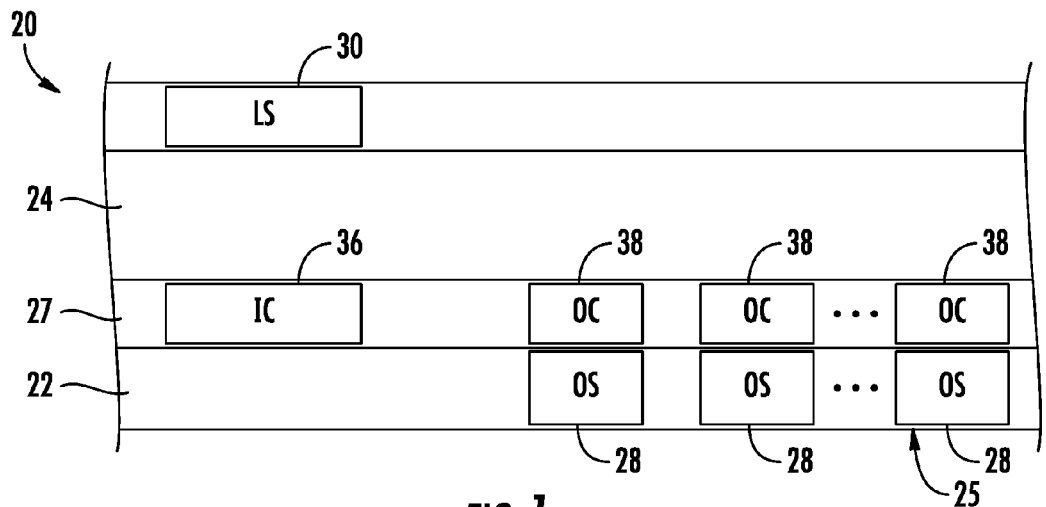
FIG. 1 is a sectional view schematically illustrating an example microfluidic fluid sensor.

FIG. 1 is a sectional view illustrating an example microfluidic fluid sensor 20. Microfluidic fluid sensor 20 integrates a spectrometer to analyze fluid and constituents of the fluid. Microfluidic fluid sensor 20 comprises substrate 22, microfluidic channel 24 and optical spectrometer 25.

Substrate 22 comprises a base or platform upon which the remaining components and associated electronics of sensor 20 are supported. In one implementation, substrate 22 comprises silicon. In other implementations, substrate 22 may comprise other materials. In one implementation, substrate 22 is provided as part of a wafer which is die cut into individual chips.

Microfluidic channel 24 comprises a conduit or passage formed upon or within substrate 22 through which fluid being sensed and analyzed is directed. Microfluidic channel 24 has a width and height, each of which is in the sub-millimeter scale. In one implementation, microfluidic channel 24 has a width and height, each having a dimension of between 5 and 200 μm and nominally between 5 and 50 μm. Although illustrated as being linear, microfluidic channel 24 may have a curved, serpentine, branched or other shape.

Optical spectrometer 25 comprises a device that detects or senses different characteristics of fluid within microfluidic channel 24 using optical spectrometry. Optical spectrometer 25 analyzes light that is passed across or through microfluidic channel 24 and which has been interacting with the fluid within channel 24. Optical spectrometer 25 analyzes such light by mode interference. In the example illustrated, optical spectrometer 25 is integrated with microfluidic channel 24 as part of a single substrate or chip. For purposes of this disclosure, the term "integrated" with respect to a chip, substrate or microfluidic channel means that a device or component is integral with the chip or substrate, or that the device or component is built into or as part of the chip or substrate in that structures of the device or component are formed or fabricated upon the chip or substrate such that they cannot be readily separated without cutting or severing portions of the chip or substrate. As a result, microfluidic fluid sensor 20 may be compact (a small form factor), less complex and self-contained.

Optical spectrometer 25 comprises waveguide 27, optical sensors 28 and light emitter or light source 30. Waveguide 27 comprises a light pipe or other structure that guides electromagnetic waves. Waveguide 27 transmits different frequencies or ranges of frequencies of light. Waveguide 27 may comprise a material or materials such as silicon nitride, silicon carbide, and gallium phosphide that facilitate transmission of light through visible and near infrared frequencies.

Waveguide 27 comprises input coupler 36 and output couplers 38. Input coupler 36 is integrated into waveguide 27 to facilitate input of light into waveguide 27. In one implementation, input coupler 36 comprises a grating coupler, wherein the grating coupler is provided with a predetermined pitch, etch angle and/or duty cycle for diffraction and/or reflection of incident light. In another implementation, input coupler 36 comprises an angled facet for directing incident light into the waveguide through total internal reflection. In one implementation, input coupler 36 facilitates the input of a particular frequency or range of frequencies into waveguide 27.

Output couplers 38 are integrated into waveguide 27 and facilitate the discharge or output of selected components, spectrums or frequencies of light being transmitted by waveguide 27. In the example illustrated, output couplers 38 comprise gratings which function as scattering objects. The output couplers 38 sample standing-wave patterns of light intensity that form in waveguide 27 due to multimode interference. This sampled light pattern is directed to the photodiodes 702. The detected light pattern may be processed digitally (using a discrete cosine transform, for example) to obtain the frequency spectrum of the light in waveguide 27.

In one implementation, output couplings 38 each comprises a scatterer that samples part of a standing-wave pattern, wherein the samples of light are directed to the corresponding optical sensors 28. In such an implementation, the scatters themselves can be made in several ways. In one implementation, the scatterers forming output couplings 38 comprise 'weak' gratings, with just 2 or 3 periods and shallowly etched grooves. Although the light scattered from these gratings is somewhat directional, the fraction of light reaching a photodiode is increased. In another implementation, the scatterers forming output couplers may comprise single grooves or holes in the waveguide 27. In this case, the light is not at all directional; however, such scatterers may be relatively easy to make and work over a broad frequency range. In yet another implementation, the scatterers forming output couplers 38 may comprise metal ridges or bumps placed on top of or underneath the waveguide 27.

Optical sensors 28 collect emitted light, energy and/or signals from corresponding output couplers 38. In the example illustrated, each optical sensor 28 is co-aligned with a corresponding one of the output couplers 38 and has substantially same spatial frequency as the corresponding output coupler 38. In one implementation, each of optical sensors 28 comprises a photoactive sensor such as a charge coupled device. One example of a charge coupled device is a photodiode. Each optical sensor 28 outputs signals based upon the received light sample from the corresponding output coupler 38. Information from all of the photodiodes is combined and analyzed together (using Fourier analysis or related type of reconstruction algorithm) to determine the frequencies of light and to detect determined properties of the fluid within microfluidic channel 24.

Light source 30 comprises a device formed upon or within substrate that directs electromagnetic radiation, such as light, across microfluidic channel 24 and ultimately to optical sensors 28. Light source 30 transmits light across microfluidic channel 24 to waveguide 27. In one implementation, light emitter 30 emits or transmits a range of frequencies and/or wavelengths of light. In one implementation light source 30 comprises a light generating device, such as a light emitting diode. In one implementation, light source 30 comprises a narrowband light source such as an ultraviolet light emitting diode. In some implementations, the ultraviolet light may be used to stimulate photoluminescence response from luminescent markers in the fluid within microfluidic channel 24. In another implementation, light source 30 comprises a broadband light source, such as a white light emitting diode, to stimulate reflection and scattering signals or photoluminescent response. In another implementation, light source 30 comprises an opening or a transparent window through which light, from an external source (either a broadband light source or a narrowband UV light source) not necessarily supported by substrate 22, illuminates microfluidic channel 24.

Figure 2:
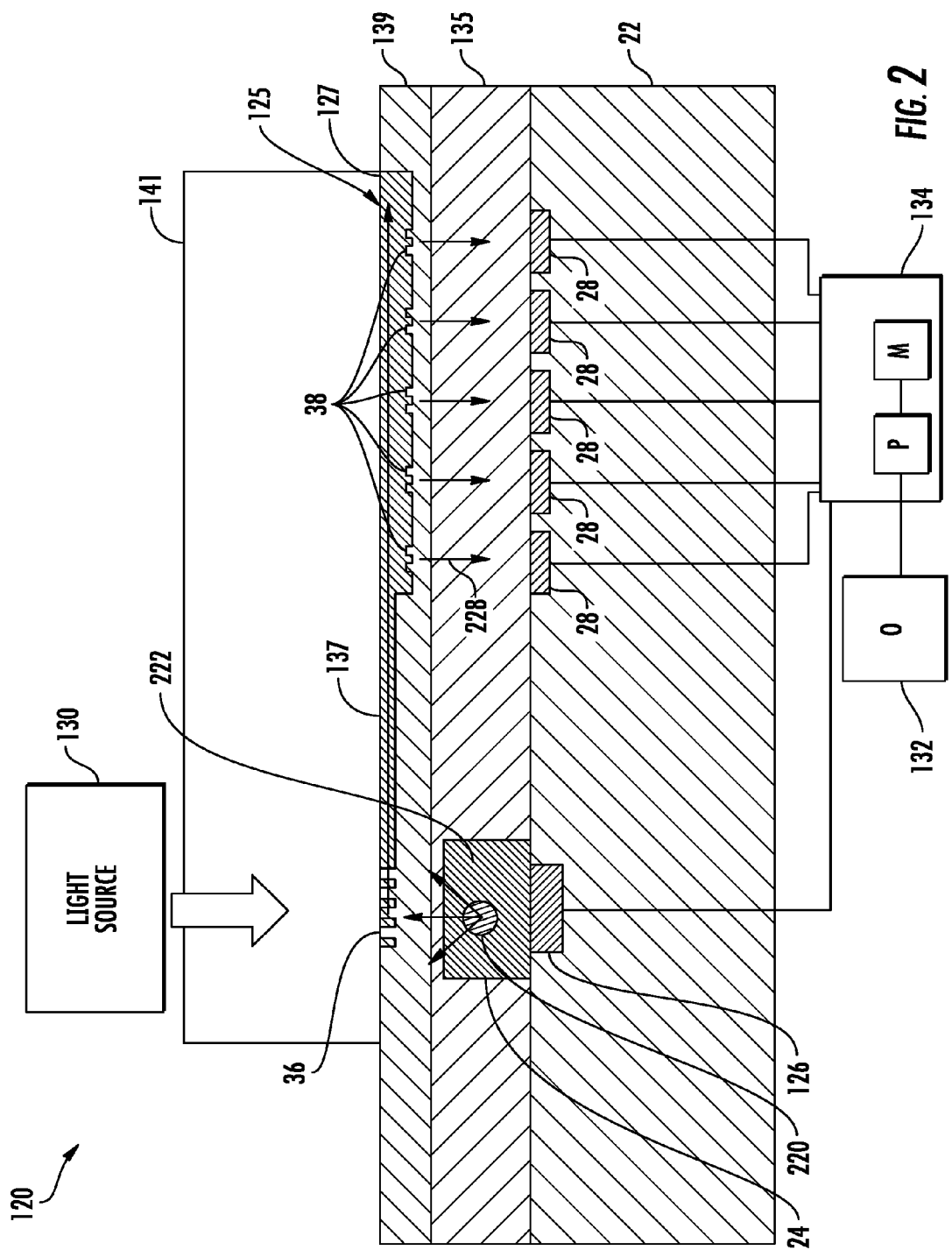
FIG. 2 is a sectional view schematically illustrating another example microfluidic fluid sensor.

FIG. 2 is a sectional view schematically illustrating microfluidic fluid sensor 120, an example implementation of microfluidic fluid sensor 20 described above. Sensor 120 comprises substrate 22, microfluidic channel 24, optical spectrometer 125, pump 126, output 132 and fluid analysis electronics 134. Substrate 22 and microfluidic channel 24 are described above with respect to sensor 20. In the sectional view illustrating FIG. 2, channel 24 is partially surrounded by a transparent substrate layer 135.

Optical spectrometer 125 is similar to optical spectrometer 25. Optical spectrometer 125 comprises waveguide 127, optical sensors 28 (described above) and light source 130. Waveguide 127 transmits different frequencies or ranges of frequencies of light. Waveguide 127 may comprise a material or materials that facilitate transmission of light through visible and near infrared frequencies, such as silicon nitride, silicon carbide, and gallium phosphide.

Waveguide 127 may comprise input coupler 36, mode filter 137 and output couplers 38. Input coupler 36 and output couplers 38 are described above. In the example illustrated, waveguide 127 is fabricated upon substrate 22, being adhered to substrate 122 by adhesion layer 139.

Mode filter 137 extends between input coupler 36 and the multimode section of waveguide 127 containing output couplers 38. Mode filter 137 transmits only a single spatial mode, and is connected to multimode waveguide 127 off of center. This may result in a well-controlled launch condition, in which a particular superposition of spatial modes is excited at the beginning of multimode waveguide 127. In one implementation, mode filter 137 also includes an integrated grating filter (not shown) to selectively remove certain frequencies of light. This may be useful, for example, in fluorescence spectroscopy, to remove the unwanted excitation light. In such an implementation, the grating filter has a predetermined pitch, etch angle and/or duty cycle to diffract and/or back reflect particular frequencies or ranges of frequencies of light. In some implementations, a particular frequency or range of frequencies may correspond to output from a laser or other light source, wherein the particular frequency or range of frequencies are not of interest in downstream analysis. The grating filter causes such frequencies to be diffracted or scattered out before entering multimode waveguide 137.

Microfluidic pump 126 comprises a device to pump or move fluid through microfluidic channel 24. In the example illustrated, microfluidic pump 126 is integrated as part of the chip and integrated as part of substrate 22. In one implementation, microfluidic pump 126 comprises an inertial pump. In one implementation, microfluidic pump 126 comprise a bubble jet inertial pump, wherein the pump produces an initially expanding bubble to move or drive adjacent fluid away from the bubble. One example of a bubble jet pump comprises a micro-heater, such as a thermal inkjet (TIJ) pump. A TIJ pump may utilize electrical resistors through which electric current is passed. The heat produced by the resistors as electric current passes through the resistors may vaporize fluid that is proximate to the resistors to create a bubble. As this bubble is initially created and expands, the bubble initially drives adjacent fluid away from the bubble. In such an implementation, microfluidic pump 126 is located along channel 24 proximate to a reservoir and distant to a different reservoir or fluid interaction component. In other words, the inertial pump is spaced from the reservoir by a distance less than one half of the length of the total fluid path between the reservoir and the other reservoir or fluid interaction component. Inertial pump may utilize inertia and momentum within a channel that is relatively narrow compared to the two reservoirs it connects to produce fluid flow. For purposes of this disclosure, the term "inertial pump" refers to a pumping device that initially drives fluid in both directions within a channel that is relatively narrow to the reservoirs it connects, but wherein the pumping device is asymmetrically positioned between the reservoirs such that the end result is fluid being driven in a direction towards the most distant of the two reservoirs.

Light source 130 comprises a source of electromagnetic radiation or light distinct from the chip and components upon substrate 22, wherein light source 130 directs light through a transparent substrate or cover layer 141 and into microfluidic channel 24. In one implementation, light source 130 comprises a light generating device, such as a light emitting diode. In one implementation, light source 130 comprises a narrowband light source that has an ultraviolet light emitting diode. In some implementations, the ultraviolet light may be used to stimulate photoluminescence response from luminescent markers in the fluid within microfluidic channel 24. In another implementation, light source 130 comprises a broadband light source, such as a white light emitting diode, to stimulate reflection and scattering signals or photoluminescent response. In still other implementations, light source 130 may be integrated as part of sensor 120 upon substrate 22. For example, in one implementation, light source 130 may be provided within the transparent cover layer 141 or upon the transparent cover layer 141.

Output 132 comprises a device by which the results of analysis of the liquid by electronic 134 are presented and/or stored. In one implementation, output 132 comprises a display screen or monitor. In one implementation, the display screen or monitor further serves as an input device, comprising a touch screen. In one implementation, output 132 comprises a memory, wherein data from the sensing and analysis of the liquid that flows through microfluidic channel 24 is stored. In one implementation, output 132 is located external or independent of the chip providing the other components of sensor 120, wherein output 132 is connected to electronics 134 in a wired or wireless fashion.

Electronics 134 may comprise a device that controls the operation of sensor 120 and receives signals from optical sensor 125 and utilize such signals (either in a raw format or after such signals have been filtered, converted or processed by electronics 134) to identify or determine characteristics of the fluid flowing through microfluidic channel 222. For example, in one implementation, electronics 134, following instructions contained in a non-transitory computer-readable medium or memory, analyzes signals received from optical sensors 28 to identify a count or number of a particular constituent or cells in the liquid or fluids flowing within microfluidic channel 624. In another implementation, electronics 634 follows instructions contained in a non-transitory computer-readable medium to identify particular constituent of the fluid or characteristics of the constituents in the fluid flowing or otherwise within microfluidic channel 24. The results of such analysis may be transmitted to output 632.

For purposes of this application, the term "processing unit" shall mean a presently developed or future developed processing unit comprising hardware (e.g., processor) that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other implementations, hard wired circuitry may be used in place of or in combination with software instructions to implement the functions described. For example, electronics 134 may be provided as part of application-specific integrated circuits (ASICs). Unless otherwise specifically noted, the controller is not limited to any specific combination of hardware circuitry and software, nor to any particular source for the instructions executed by the processing unit.

In one implementation, the energy, light, and/or signals aliased to the lower spatial frequency and emitted by the gratings of output couplers 38 and that are collected (e.g., captured) by individual detectors, such as the individual optical sensors 28 (e.g., photoactive sensors) and in some implementations, the characteristics of the input light provided by light source 130, are analyzed and/or calibrated by electronic 134 (e.g., using Fourier analysis) to determine particular characteristics (e.g., a spectrum) that identify characteristics of the fluid being sensed.

In one implementation, the electronics comprises a memory storing a predetermined lookup table that correlates different electrical signals from optical sensors 28 to different fluid constituent counts and/or different fluid constituent characteristics. In such an implementation, the processing unit identifies fluid constituent counts or fluid constituent characteristics by comparing the electrical signals from sensors 28 to the different values in the lookup table. In one implementation, electronics 34. In another implementation, electronics 134 utilizes values based upon the different electrical parameter signals as part of a formula to calculate or estimate the fluid flow rate.

In one implementation, fluid sensor 120 is entirely contained or integrated upon substrate 22 or the circuit chip containing microfluidic channel 24. For example, in one implementation, electronics 134 is integrated as part of the chip or substrate 22 in or on which microfluidic channel 24 is provided. In yet other implementations, portions of fluid sensor 120 are distributed among separate substrates or devices. For example, in one implementation, output 132 and electronics 134 are provided by a separate device that is electrically connected to electrical contacts or electrical contact pads provided on the chip containing the remaining elements of sensor 120.

Figure 3:
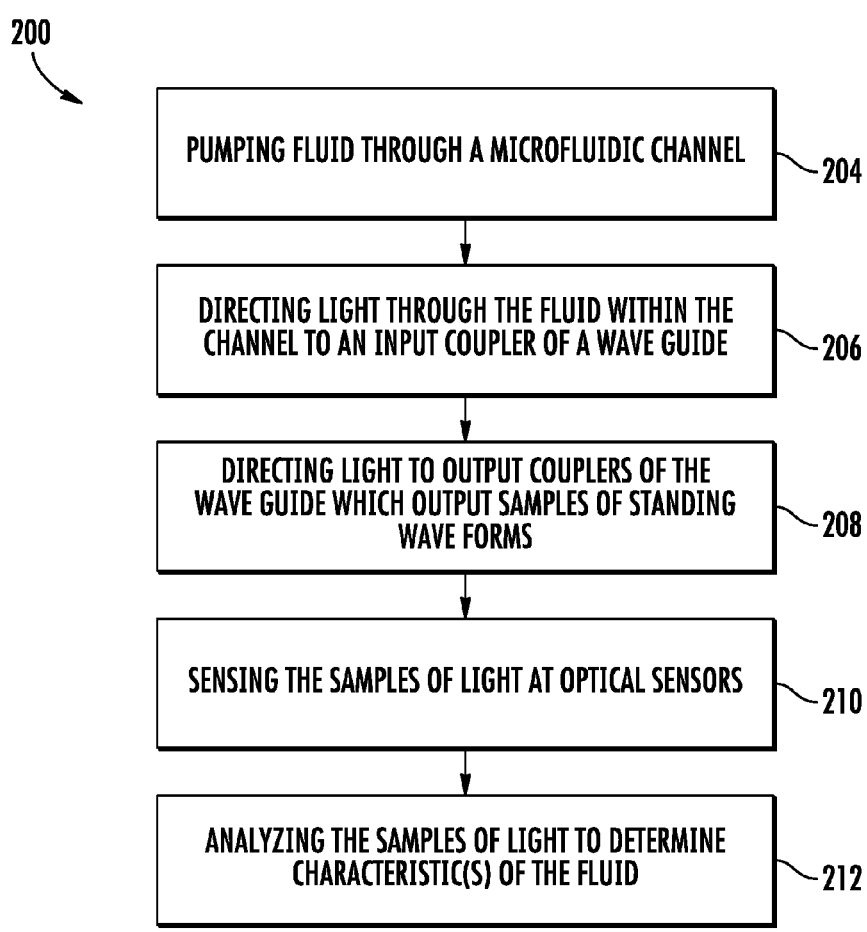
FIG. 3 is a flow diagram of an example method for sensing fluid using a microfluidic fluid sensor.

FIG. 3 is a flow diagram of an example method 200 that may be carried out by system 120 for sensing and analyzing fluid. As indicated by block 204, electronics 134 outputs control signals directing my fluid pump 126 to move or pump fluid through channel 24. As indicated by block 206, light source 130 directs light through the fluid within channel 24 to an input coupler, such as input coupler 36, of waveguide 127. As schematically illustrated by FIG. 2, light is reflected and/or refracted off of constituents 220 carried by the fluid 222, wherein the light is incident upon input coupler 36. In other implementations, input coupler 36 is located on an opposite side of microfluidic channel 24 as light source 130, wherein light from light source 130 passes through and across channel 24 to input coupler 36.

As indicated by block 208, waveguide 127 directs the light to output couplers 38, wherein each output coupler may sample a standing wave pattern and direct the sample in the optical intensity towards a corresponding optical sensor 28. As indicated by arrows 28, the samples of light are transmitted to corresponding optical sensors 28.

In one implementation, the light is transmitted through a mode filter 137 that transmits only a single spatial mode and that filters out or removes selected frequencies from the light being transmitted by multimode waveguide 127 off of center. This results in a well-controlled launch condition, in which a particular superposition of spatial modes is excited at the beginning of multimode waveguide 127.

As indicated by block 210, optical sensors 28 sense the light received from output couplers 38. Optical sensors 28 output electrical signals which are transmitted to electronics 134. In one implementation, substrate 22 comprises electrical contact pads by which electronics 134, external substrate 22 or the chip formed by substrate 22, are connected. In another implementation, electronics 134 are integrated upon substrate 22.

As indicated by block 212, electronics 134 analyzes the standing wave forms of light, represented by little signals from optical sensors 28, to determine characteristics of the fluid. In one implementation, the samples from the standing-wave pattern are converted to spectral information using Fourier analysis of the electronic signals (discrete-cosine transform, for example) or more complicated reconstruction methods (based on least-squares, for example) that can incorporate sensor calibration data. Electronics 134 determines characteristics of the fluid based upon the spectral information. Such characteristics may include a count or number of cells, particles or constituents of the fluid, a size or density of such cells, particles or constituents and/or in identification of the particular cells, particles or constituents. The results of the analysis are stored and/or presented on output 632.

Figure 4:
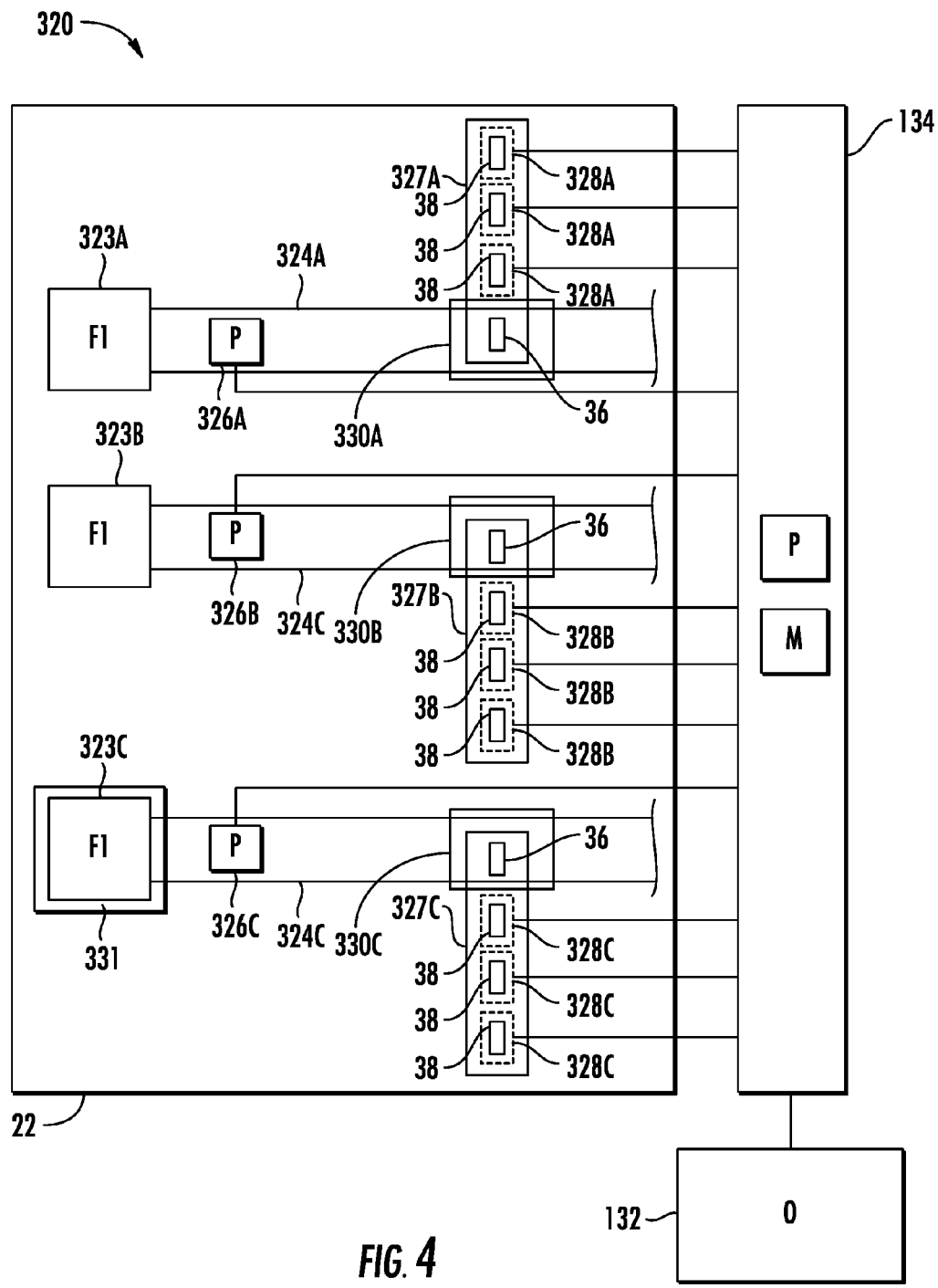
FIG. 4 is a top view schematically illustrating another example microfluidic fluid sensor.

FIG. 4 is a top view schematically illustrating microfluidic fluid sensor 320, another example implementation of microfluidic fluid sensor 20. Microfluidic fluid sensor 320 is similar to fluid sensor 120 except that fluid sensor 320 senses fluid within multiple channels. Microfluidic fluid sensor 320 comprises substrate 22, fluid inputs 323A, 323B, 323C (collectively referred to as inputs 323), microfluidic channels 324A, 324B, 324C (collectively referred to as channels 324), microfluidic pumps 326A, 326B, 326C (collectively referred to as pumps 326), waveguide 327A, 327B, 327C (collectively referred to as waveguide 327), optical sensors 328A, 328B, 328C (collectively referred to as optical sensors 328), light sources 330A, 330B, 330C (collectively referred to as light sources 330), pillar filter 331, output 132 and electronics 134. Fluid inputs 323 comprise passages or ports by which fluid is introduced to channel 324. In the example illustrated, channel 324A and 324B channel fluid to side-by-side spectrometers. Channel 324C comprises a reference channel. In the example illustrated, pillar filter 331 filters fluid introduced through a fluid import 323C to protect channel 324C from access of cells.

Channels 324 are each similar to channel 24 described above. Although channels 324 are illustrated as being linear, in other implementations, channel 324 may have other shapes. Pumps 326 are each similar to pump 126 described above. Likewise, waveguide 327 is similar to waveguide 127 described above. Waveguide 327 comprises an input coupler 36 and multiple associated output couplers 38. Optical sensors 328 are each similar to optical sensors 28 described above.

Light sources 330 comprises a source of electromagnetic radiation or light, wherein each light source 130 may direct light into its respective one of microfluidic channels 324. In one implementation, each light source 130 comprises a light generating device, such as a light emitting diode. In one implementation, light source 330A comprises a narrowband light source that has an ultraviolet light emitting diode. In some implementations, the ultraviolet light may be used to stimulate photoluminescence response from luminescent markers in the fluid within microfluidic channel 24. Light source 330B comprises a broadband light source, such as a white light emitting diode, to stimulate reflection and scattering signals or photoluminescent response. Light source 330C provide light for reference channel 324C. Reference channel 324C facilitate differential photoluminescent single detection using broadband illumination provided by light source 330C. The provision of reference channel 324C and its associated components increases the robustness of cell detection and differentiation.

Output 132 and electronics 134 are described above. In operation, upon analysis initiation, such as upon sample fluids being introduced through fluid inputs 323, electronics 134 outputs control signals actuating pumps 326 to move fluid through the respective channels 324. Light from light sources 330 is directed into channel 324 where it is incident upon the fluid. Input couplers 36 receive the incident light and direct the light to output couplers 38 which spectrally separate the light in the various frequencies or components that are detected by optical sensors 328. Signals from optical sensors 328 are received by electronics 134 and analyzed, such as through Fourier analysis, to detect to determine characteristics of the fluid. The detection of such fluid characteristics may involve detecting photoluminescent response from luminescent markers in the fluid and detection of fluid constituent reflection or scattering. Such signals may be compared to the fluid contained within the reference channel 324 that has been filtered by pillar filter 331. The results of such analysis are presented and/or stored on output 132.

Figure 5:
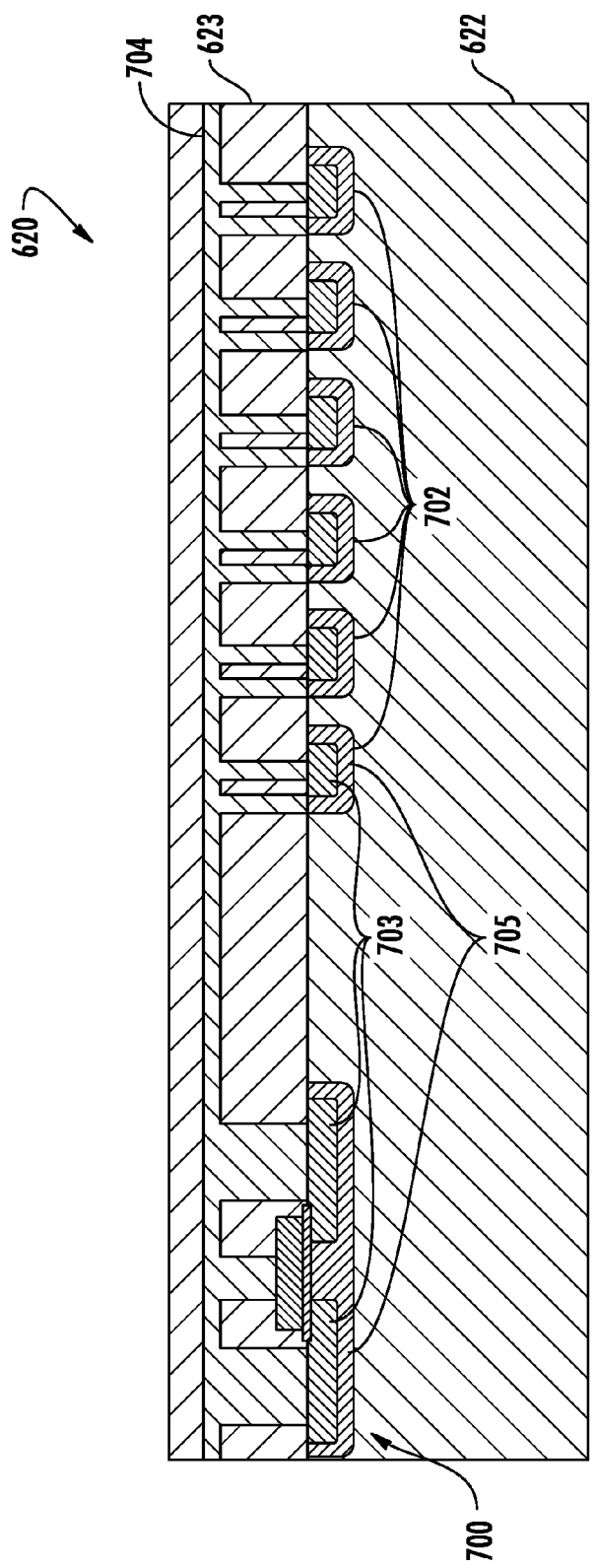
FIGS. 5-16 are sectional views illustrating formation of another example microfluidic fluid sensor.
Figure 16:
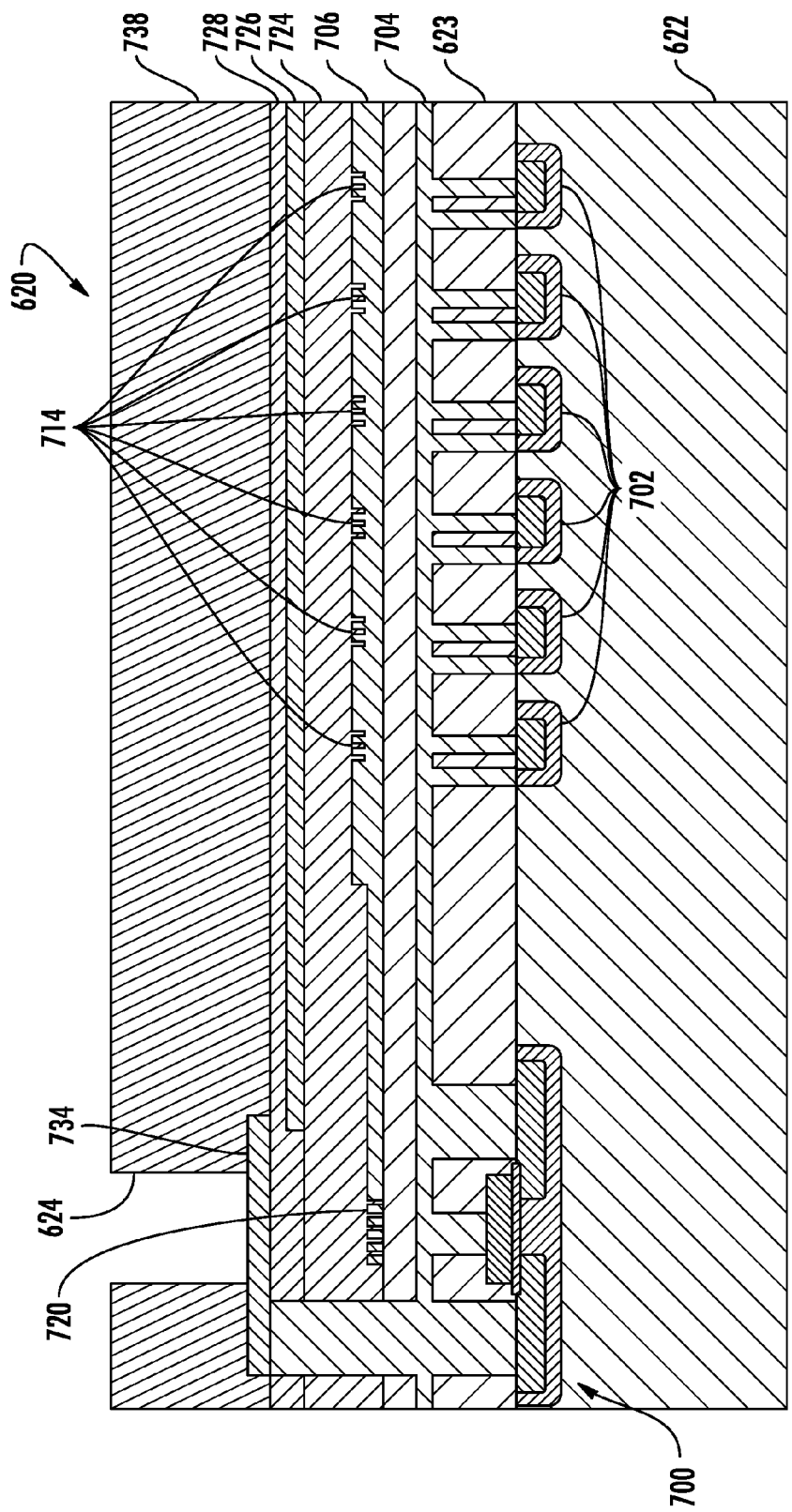
Figure 17:
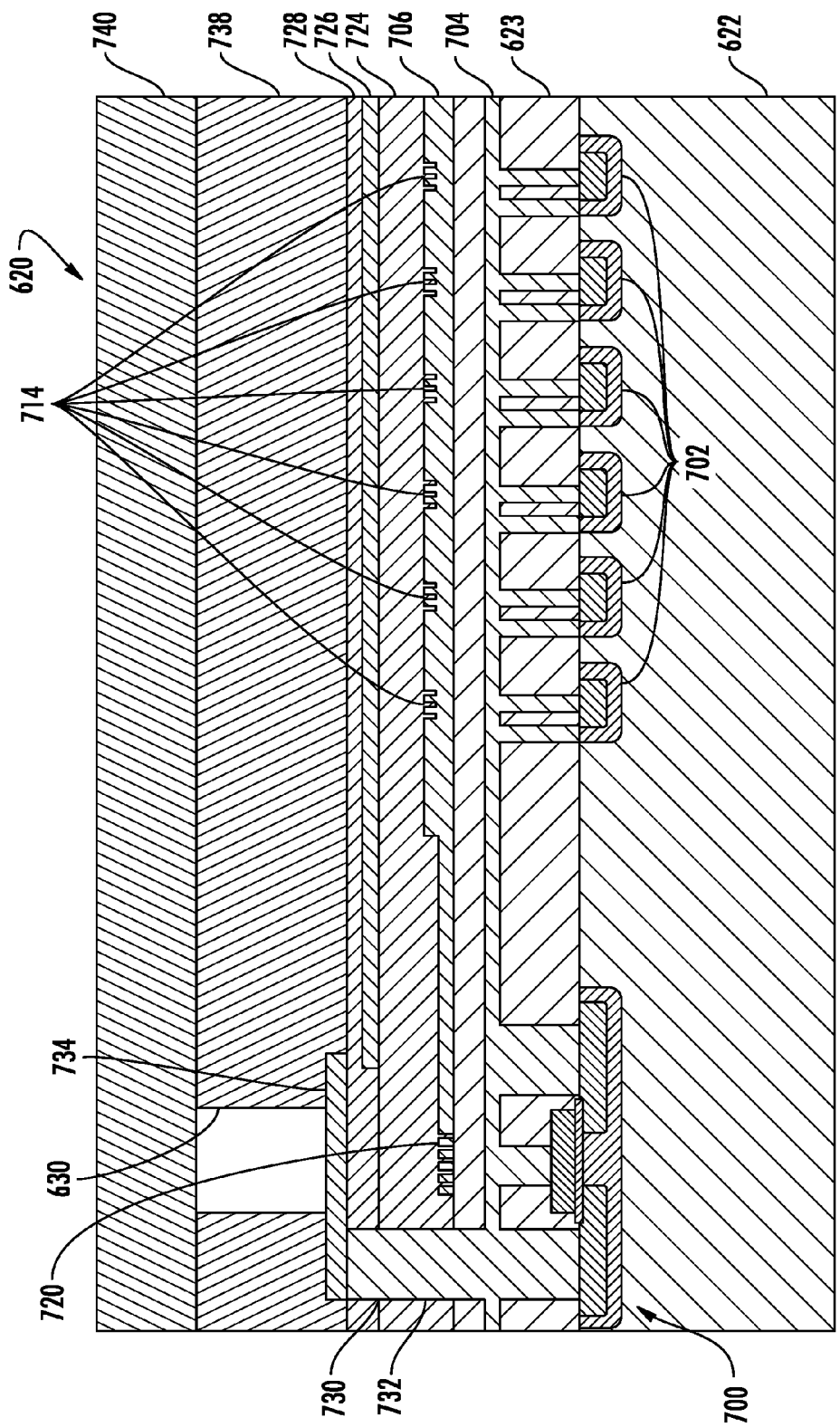
FIG. 17 is a section view illustrating completion of the microfluidic fluid sensor fabricated in FIGS. 5-16.
Figure 18:
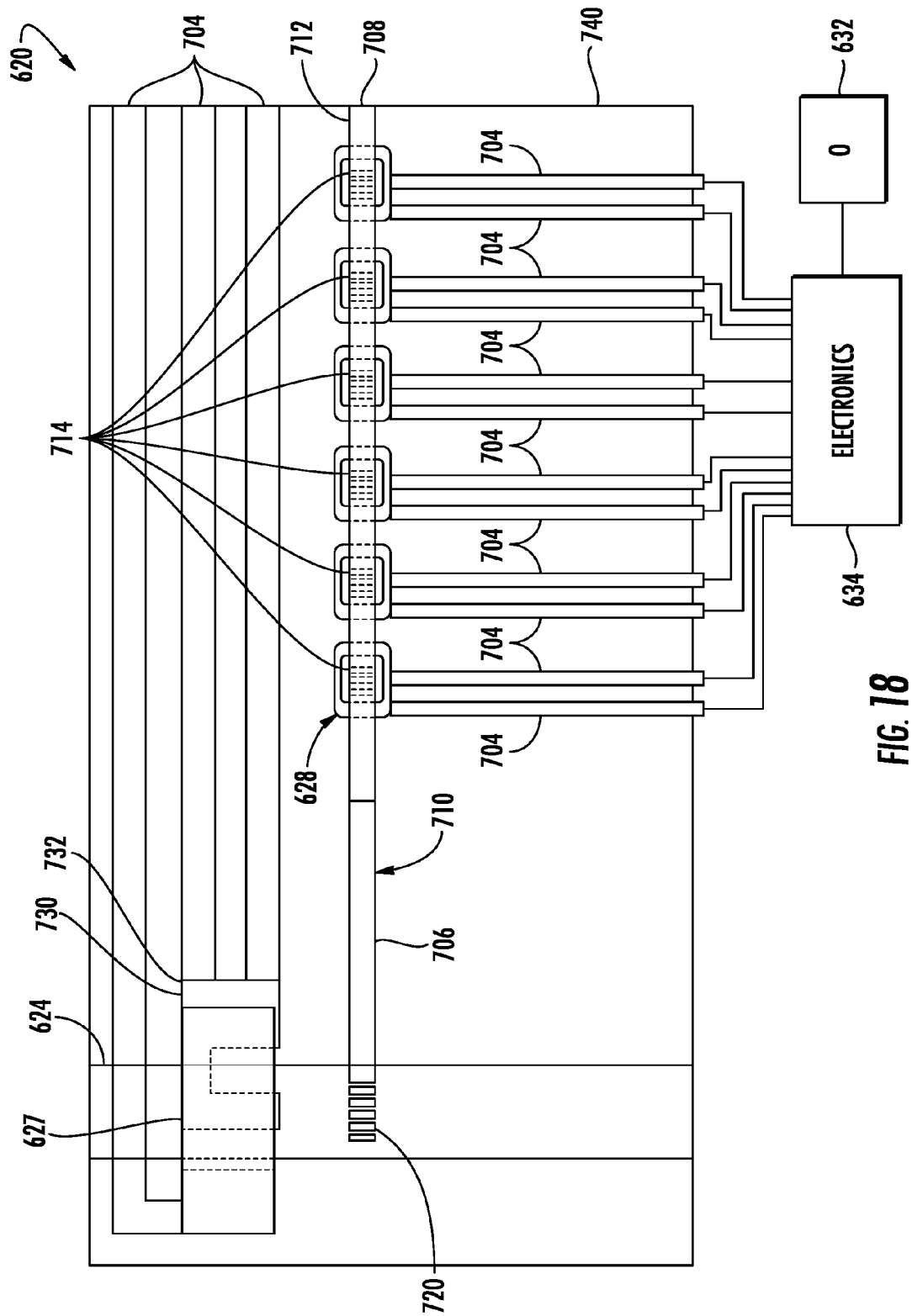
FIG. 18 is a top view of the microfluidic sensor of FIG. 18.

FIGS. 5-18 illustrate the formation of an example microfluidic optical fluid sensor 620 (shown completed in FIGS. 17 and 18). As shown by FIG. 5, semiconductor fabrication processes are carried out with respect to a substrate 622 to form a field effect transistor 700 (comprising a source, a drain, a gate and a semiconductor channel) and an array of photodiodes 702 upon substrate 622. In the example illustrated, portions of the transistor 700 and the photodiodes 702 each includes concurrently formed p-type doping regions 703 and n-type doping regions 705. Metal/dielectric layers 623 are formed or patterned upon substrate 622 and comprise various electrical interconnects 704 for transistor 700 and photodiodes 702. In the example illustrated, complementary metal-oxide-semiconductor processes are employed to form such structures. In the example illustrated, substrate 622 may comprise a silicon substrate. In other implementations, other semiconductor processes may be employed and substrate 622 may be formed from and/or comprise other materials.

Figure 6:
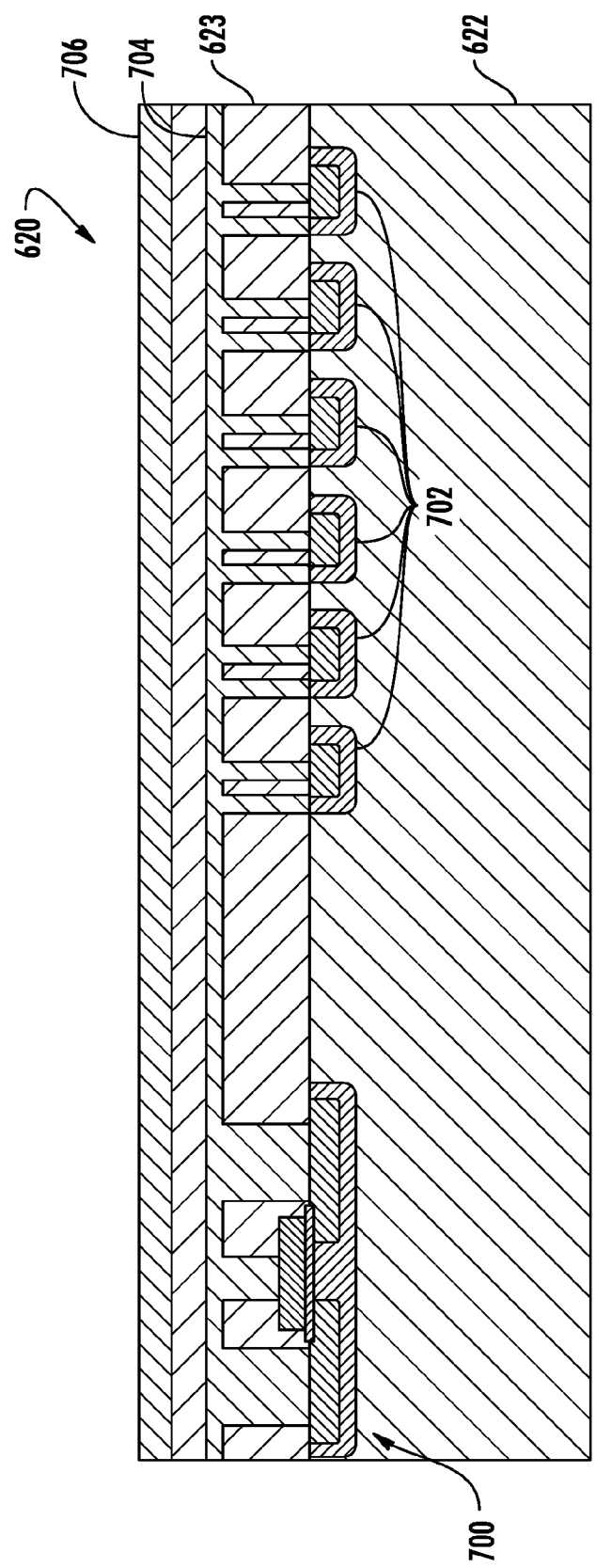

As illustrated by FIG. 6, sensor 620 employs a waveguide to transmit light to the form photodiodes 702. In the example illustrated, the layer of material forming a waveguide layer 706 is deposited and patterned upon the metal/dielectric layer 623. In one implementation, the material for the waveguide layer 706 comprises silicon nitride. In one implementation, the silicon nitride or other material forming waveguide layer 706 is deposited using plasma enhanced chemical vapor deposition or low-pressure chemical vapor deposition. In other implementations, the waveguide layer 706 may be formed from other materials and may be formed in other fashions.

Figure 7:
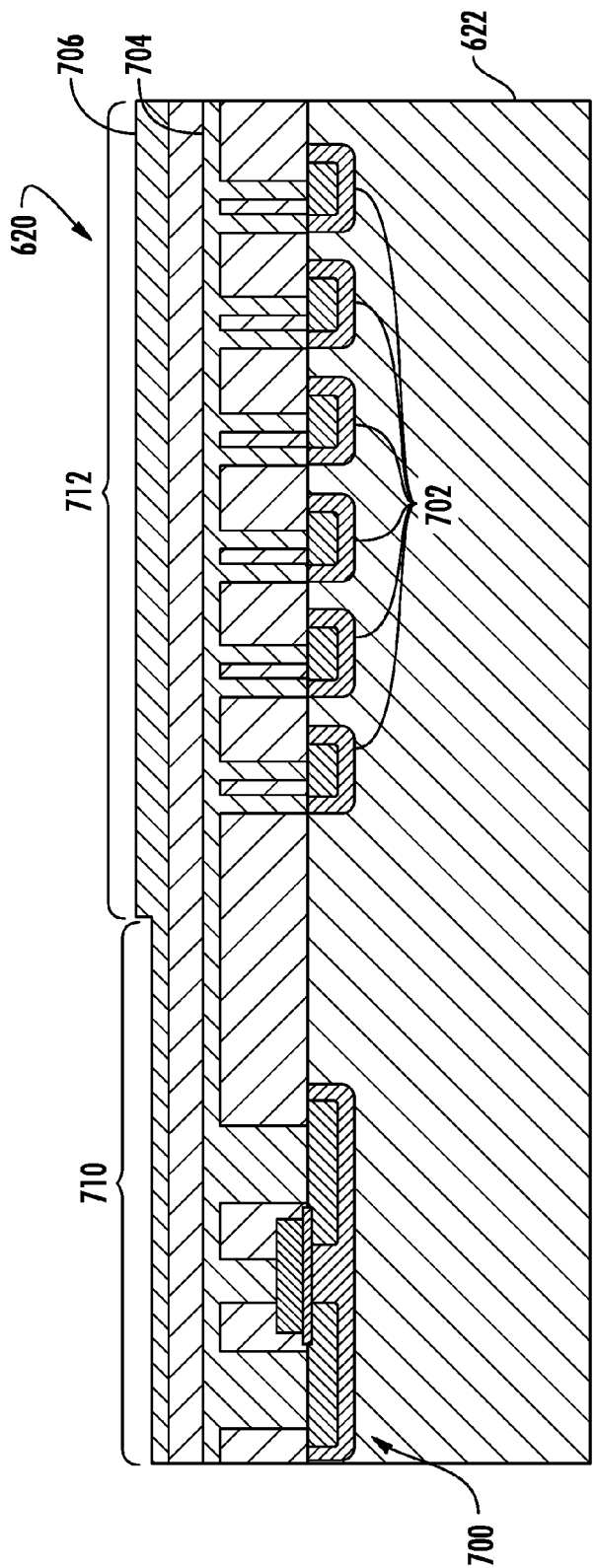
Figure 8:
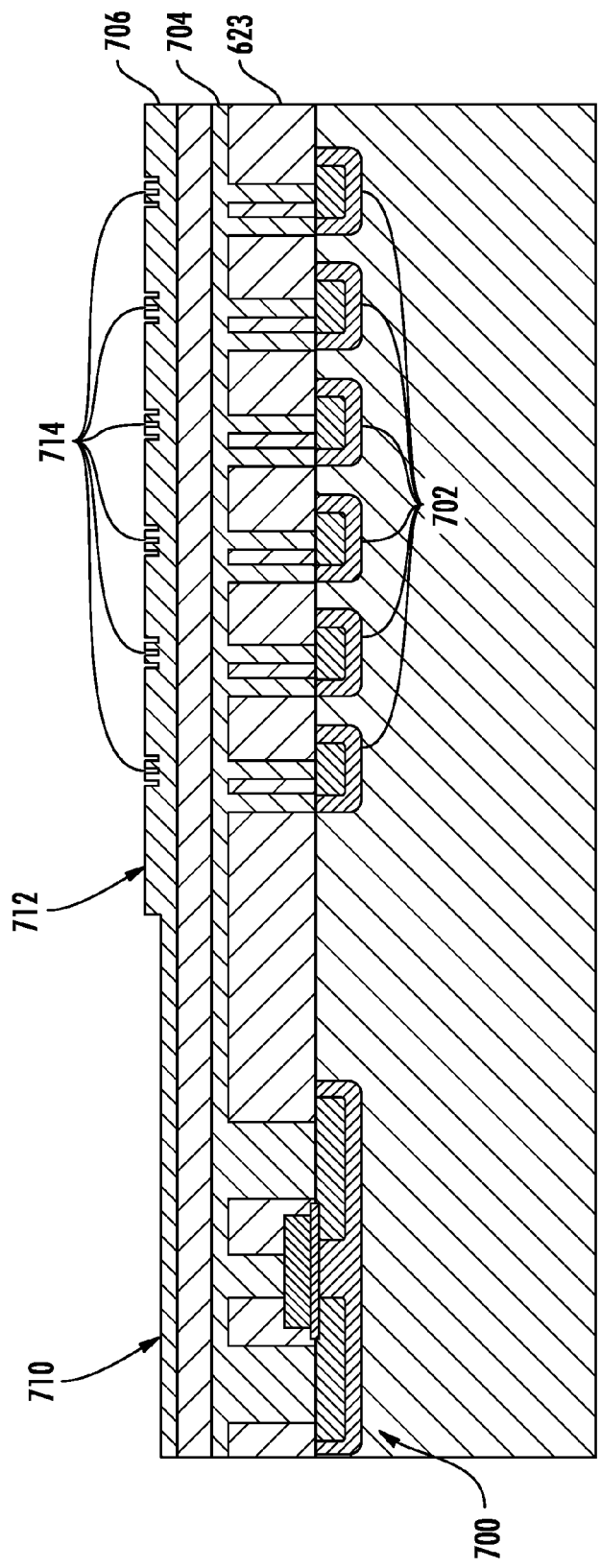

As illustrated by FIG. 7, portions of waveguide layer 706 are removed to form or define a single mode region 710 and a multi-mode region 712. In the example illustrated, portions of waveguide layer 706 are removed through etching to define such regions. As illustrated by FIG. 8, portions of multimode region 712 further removed to form or define various output couplers or gratings 714. Output couplers or gratings 714 comprise scattering objects by which a standing wave intensity pattern of light traveling through waveguide layer 206 is sampled and directed to corresponding optical sensors in the form of photodiodes 702. In one implementation, such gratings 714 are spaced at regular intervals (a spatial frequency) along waveguide layer 706. Since the gratings 714 are on the top surface, they may sample the electric field near the top of the waveguide.

In one implementation, gratings 714 function as scattering objects, by which gratings 714 sample standing-wave patterns of light intensity that form in waveguide 706 due to multimode interference. This sampled light pattern is directed to the photodiodes 702. The detected light pattern may be processed digitally (using a discrete cosine transform, for example) to obtain the frequency spectrum of the light in waveguide 27.

Figure 9:
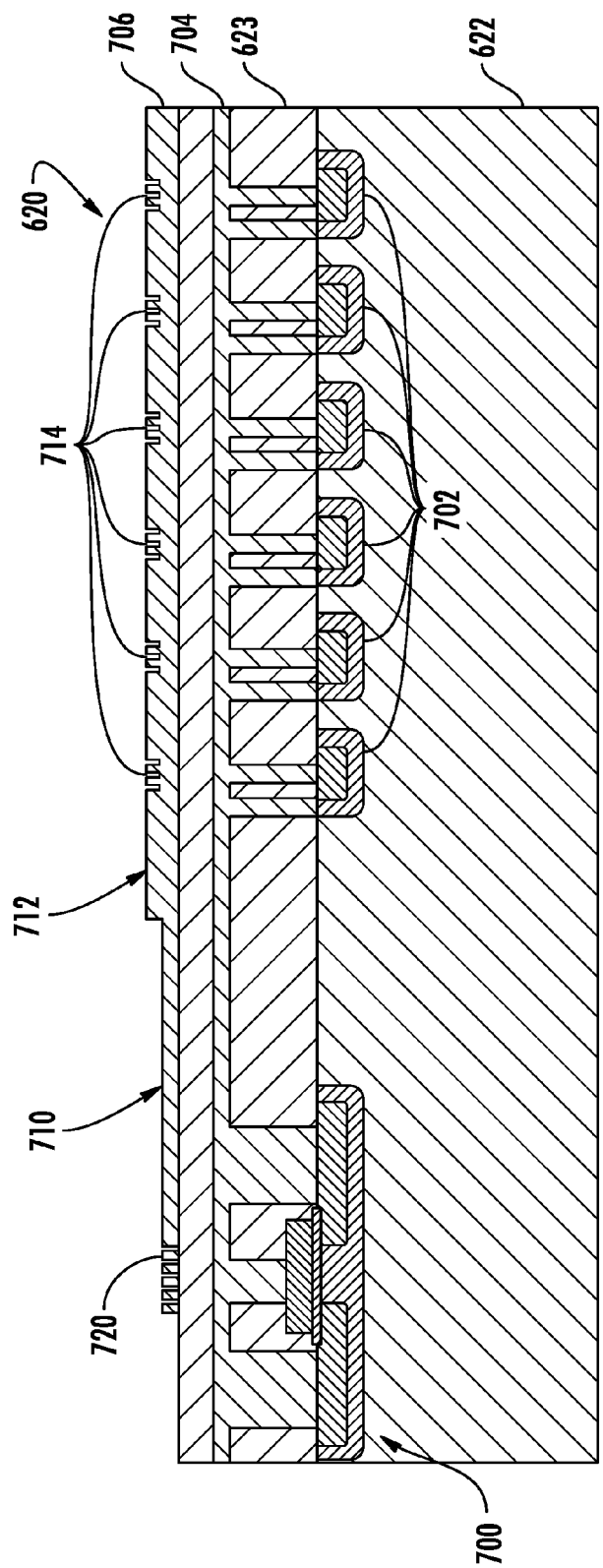

As illustrated by FIG. 9, additional portions of the waveguide layer 706 are further removed so as to form input coupler 720 and define the side walls of the waveguides. In the example illustrated, input coupler 720 comprises a grating coupler. The grating coupler serving as input coupler 720 may have a predetermined pitch, etch angle, and/or duty cycle for diffraction and/or reflection of incident light, such as incident light from a light emitter, wherein the incident light may be redirected so as to travel in and intended direction along waveguide layer 706 to gratings 714.

Figure 10:
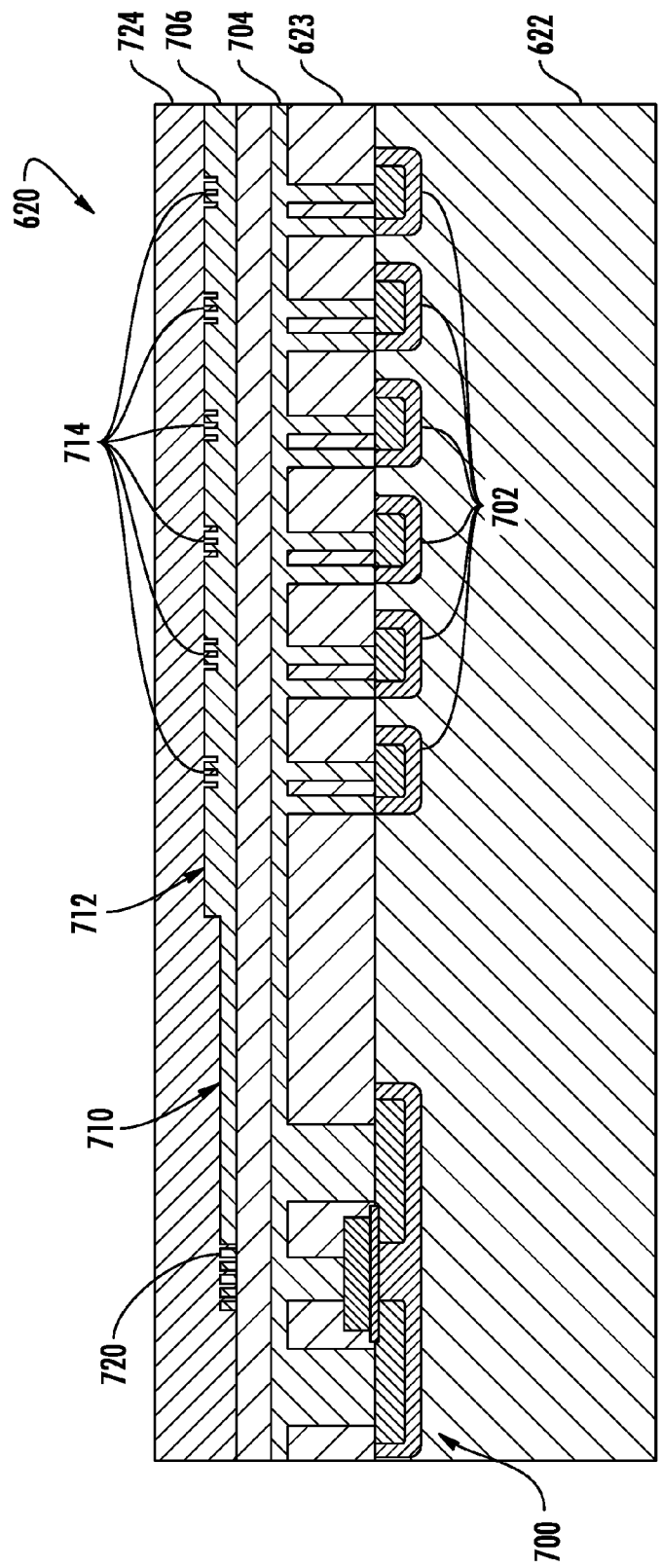
Figure 11:
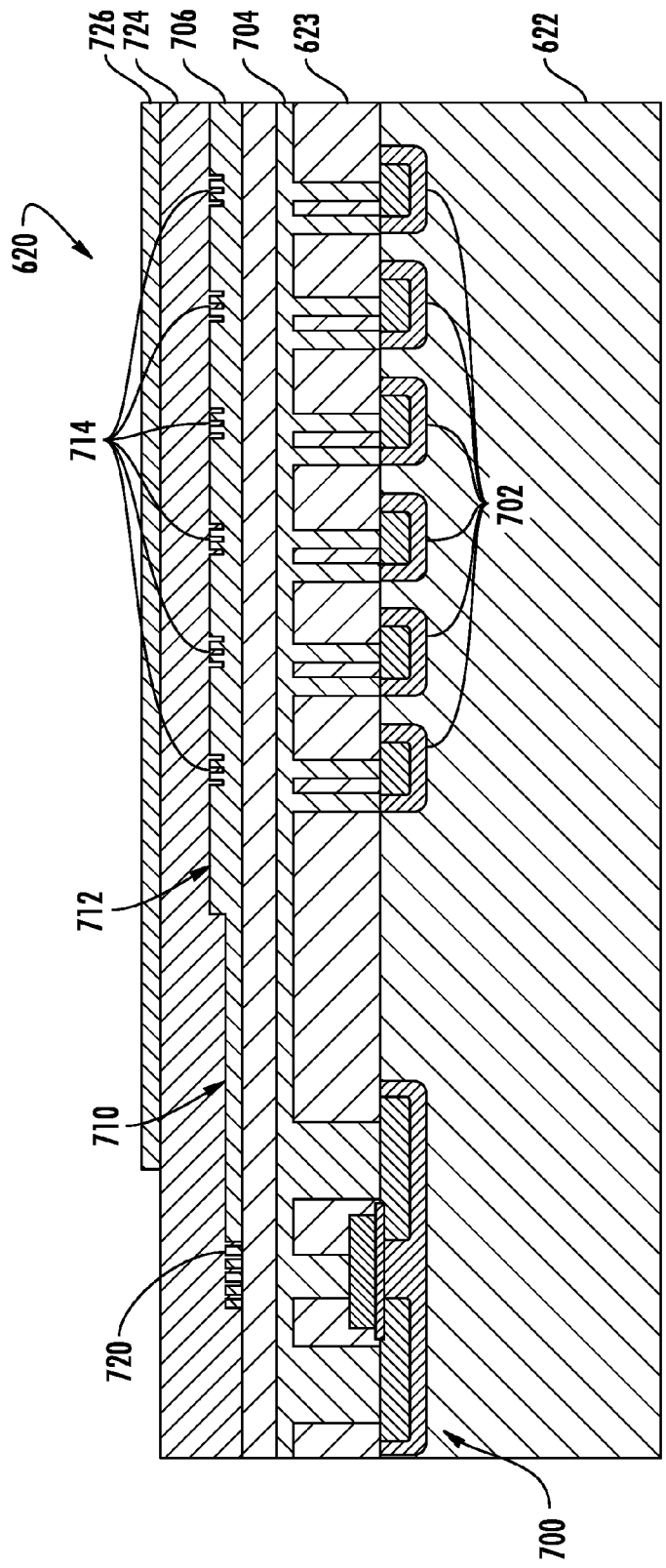
Figure 12:
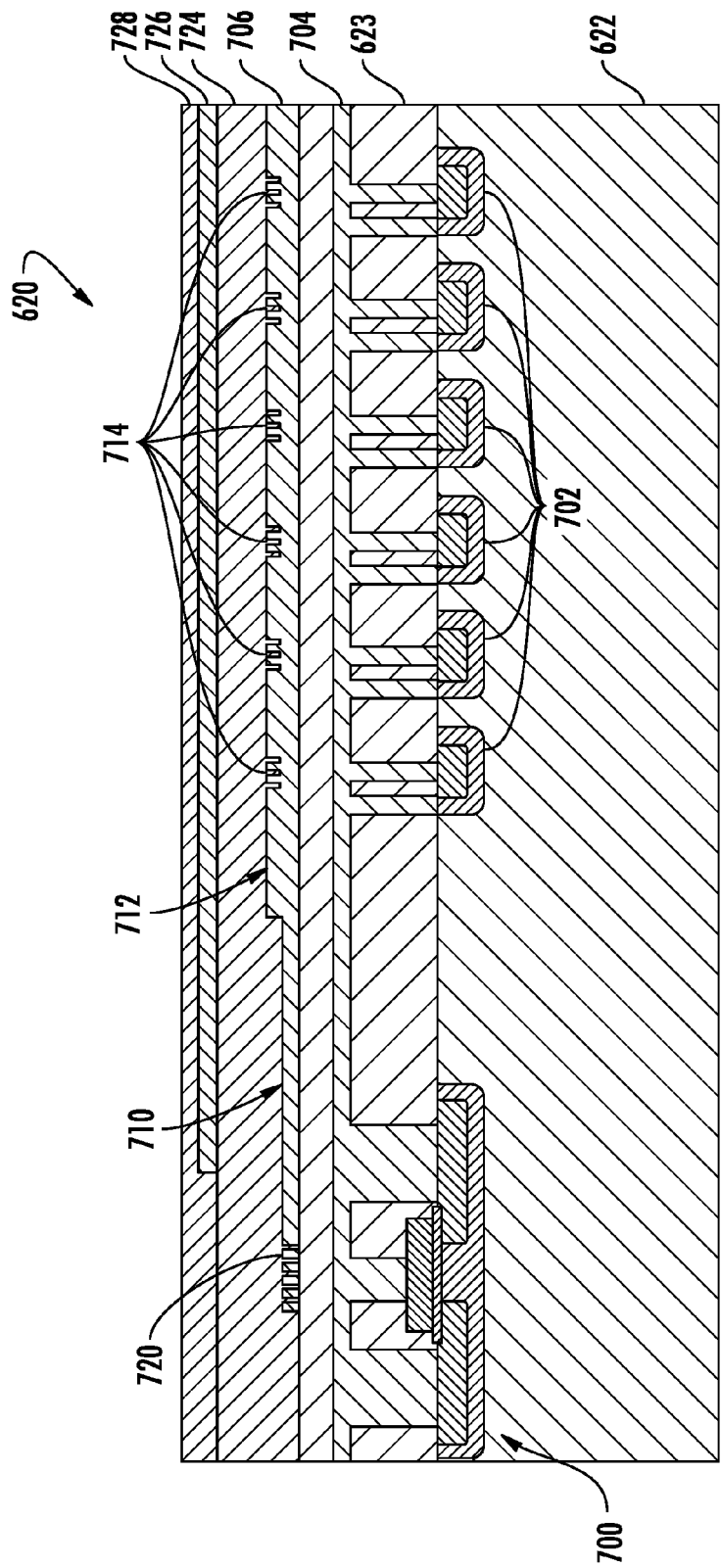
Figure 13:
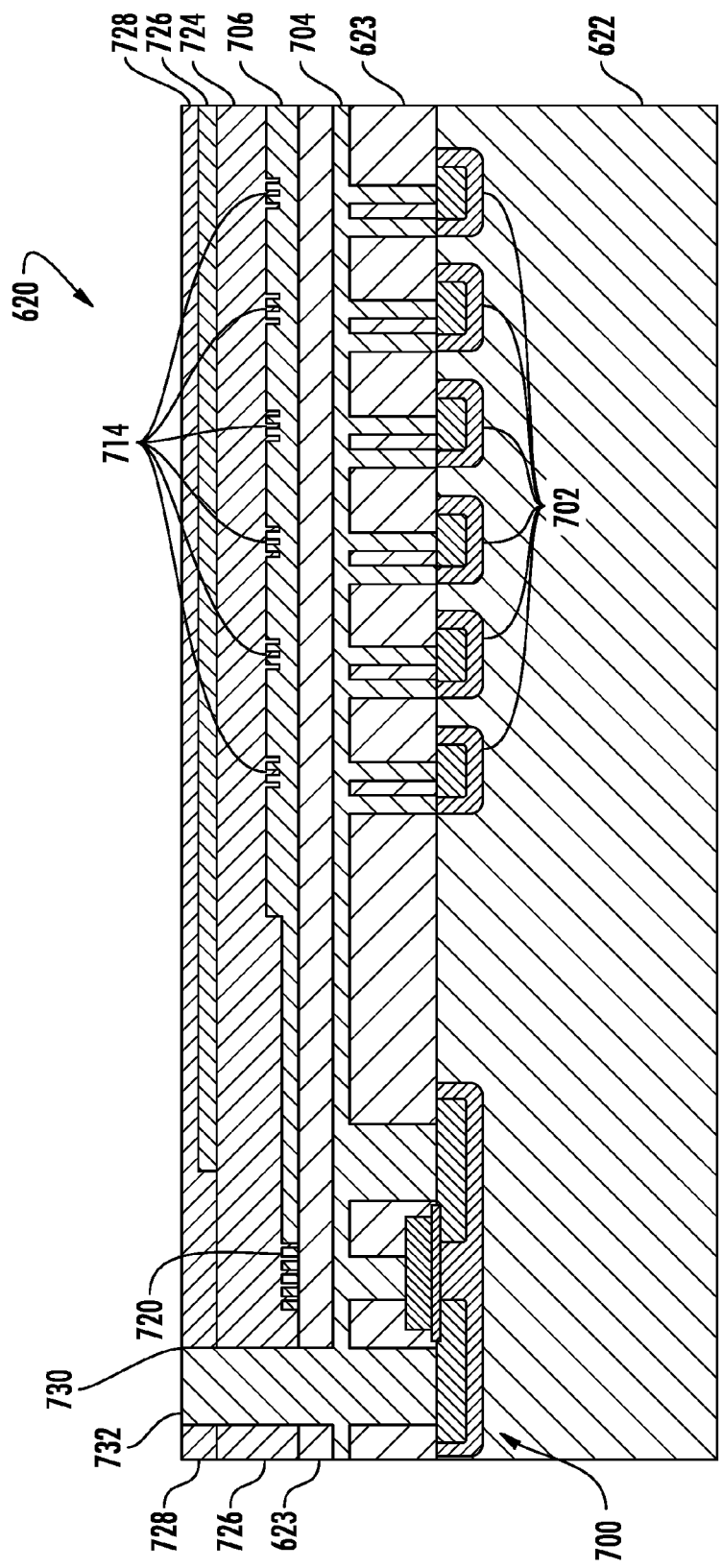
Figure 14:
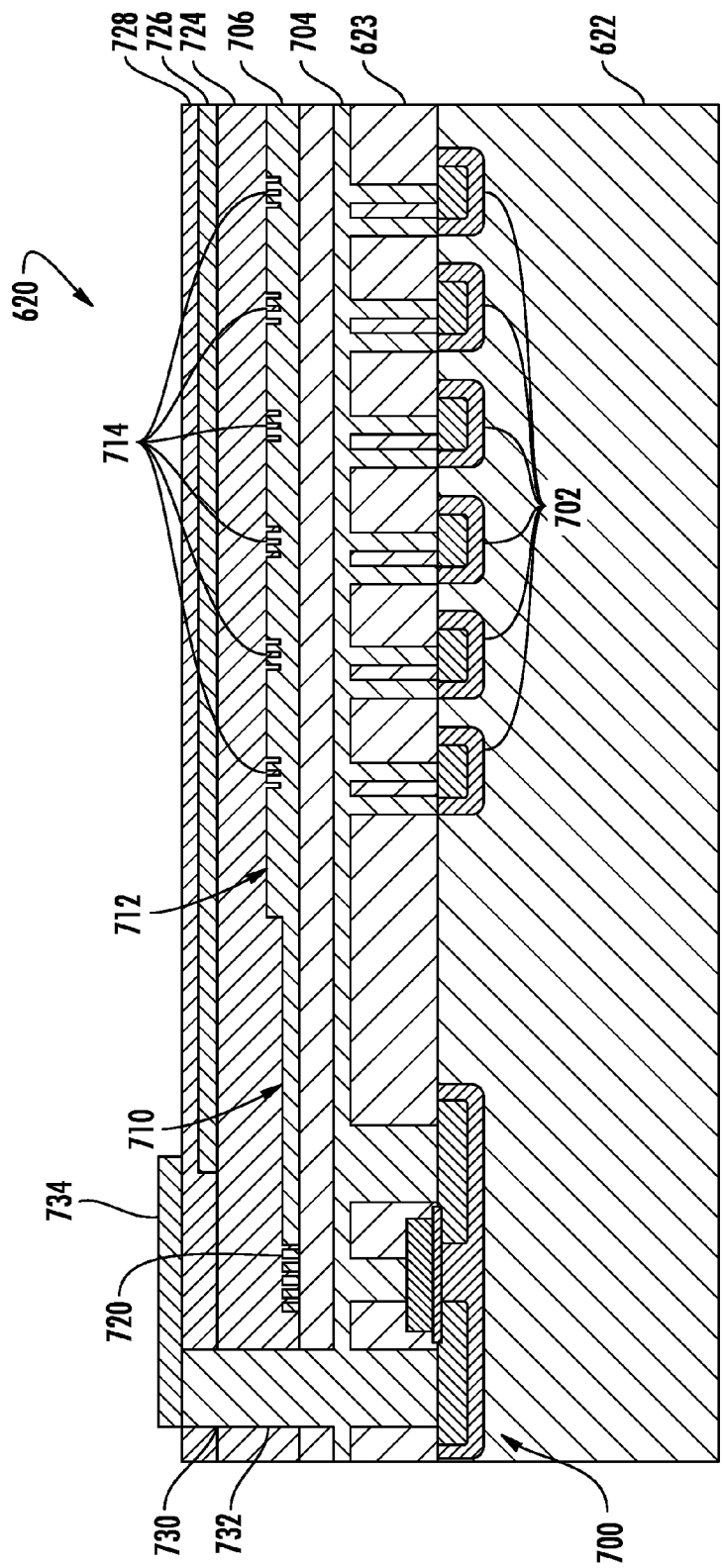
Figure 15:
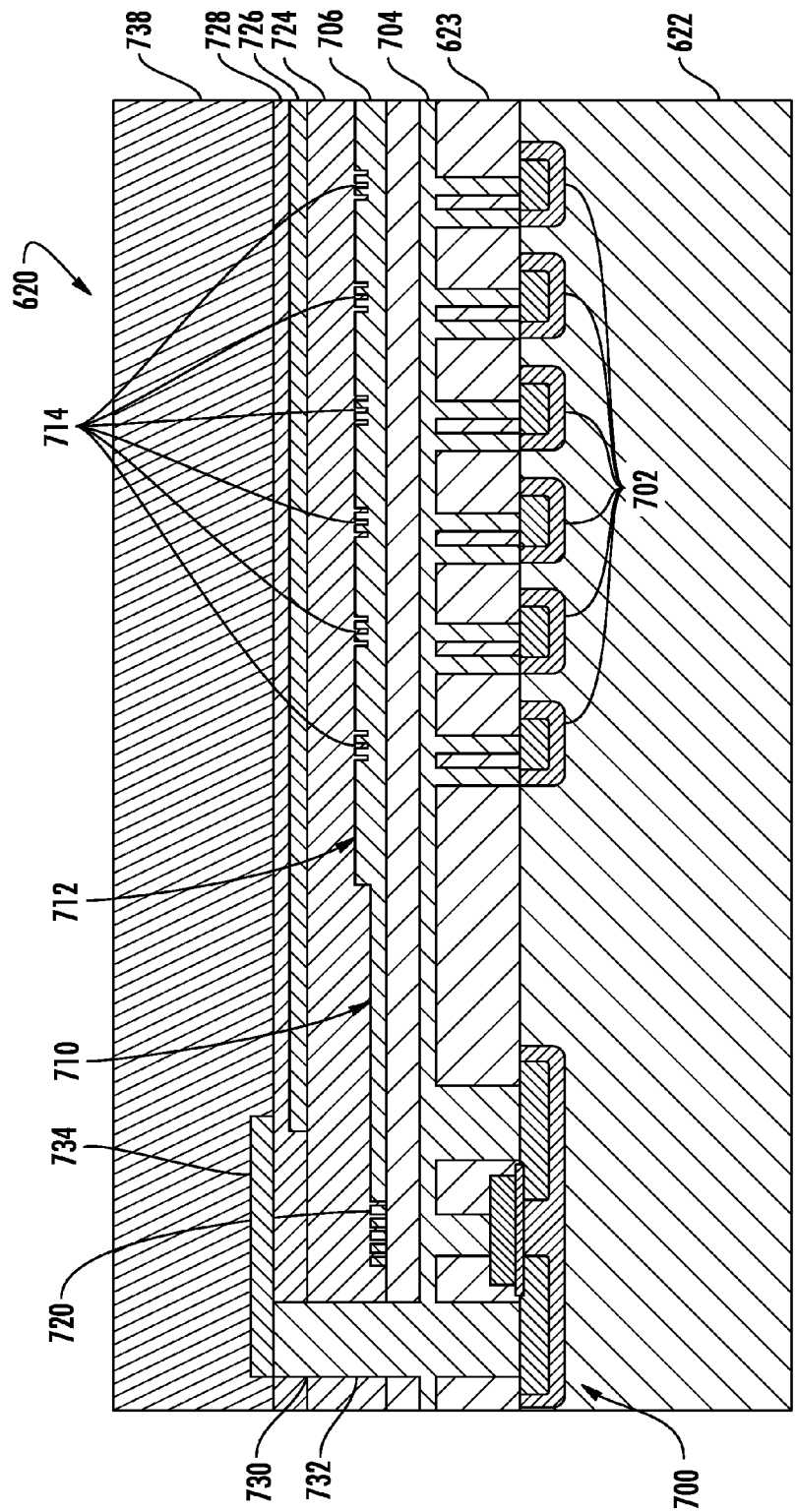

As illustrated by FIG. 10, upon the formation of input coupler 720 and the gratings 714 serving as output couplers, the top dielectric layer 724 is applied or deposited upon waveguide layer 706. As illustrated by FIG. 11, a metal reflective or light shield layer 726 is deposited upon the top dielectric layer 724 in regions opposite to gratings 714 serving as output couplers. As illustrated by FIG. 12, an additional dielectric layer 728 is deposited upon the metal reflective or light shield layer 726. As illustrated by FIG. 13, layers 728, 724 and 623 are etched to form via 730. As illustrated by FIG. 14, the thermal inkjet resistor 734 is formed upon dielectric layer 728 and is electrically connected to transistor 700 through via 730. As illustrated by FIG. 15, a channel forming layer 738 is formed upon layer 728 and upon resistor 734. In one implementation, layer 738 comprises a layer of transparent photoresist material such as an epoxy-based negative photoresist such as SU-8 (Bisphenol A novolac epoxy that has been dissolved in organic solvent such as gamma butylaractone GBL or cyclopentanone). As illustrated by FIG. 16, layer 738 is further exposed and developed to form microfluidic channel 624. Lastly, as illustrated by FIG. 17, a transparent cover layer 740 is formed or deposited on layer 738 over or across microfluidic channel 624. In some implementations, a lens may additionally be formed opposite to or over microfluidic channel 624.

FIG. 18 is a top view of the completed microfluidic optical fluid sensor 620. As shown by FIG. 18, sensor 620 comprises microfluidic channel 624, bubble jet inertial pump 626, optical sensor 628, light source 30 (shown in FIG. 2), output 632 and control and analysis electronics 634. Microfluidic channel 624, bubble jet inertia pump 626, optical sensors 628 the light emitter 30 perform and carry out the general functions described above with respect to microfluidic channel 24, bubble jet inertia pump 26, optical sensor 28 and light emitter 30 described above with respect to system 20. Each of such components is integrally formed upon the sensing chip (shown in FIG. 19) which may comprise the various layers comprising substrate 622.

Output 632 may comprise a device by which the results of analysis of the liquid by electronic 634 are presented and/or stored. In one implementation, output 632 comprises a display screen or monitor. In one implementation, the display screen or monitor further serves as an input device, comprising a touch screen. In one implementation, output 632 comprises a memory, wherein data from the sensing and analysis of the liquid that flows through microfluidic channel 624 may be stored. In one implementation, output 632 is located external or independent of the chip providing the other components of sensor 620, wherein output 632 is connected to electronics 634 in a wired or wireless fashion.

Electronics 634 may comprise a device that controls the operation of sensor 620 and receives signals from optical sensor 625 and utilizes such signals (either in a raw format or after such signals have been filtered, converted or processed by electronics 634) to identify or determine characteristics of the fluid flowing through microfluidic channel 624. For example, in one implementation, electronics 634, following instructions contained in a non-transitory computer-readable medium or memory, analyzes signals received from optical sensor 628 to identify a count or number of a particular constituent or cells in the liquid or fluids flowing within microfluidic channel 624. In another implementation, electronics 634 follows instructions contained in a non-transitory computer-readable medium to identify particular constituent of the fluid or characteristics of the constituents in the fluid flowing or otherwise within microfluidic channel 624. The results of such analysis are transmitted to output 632.

Figure 19:
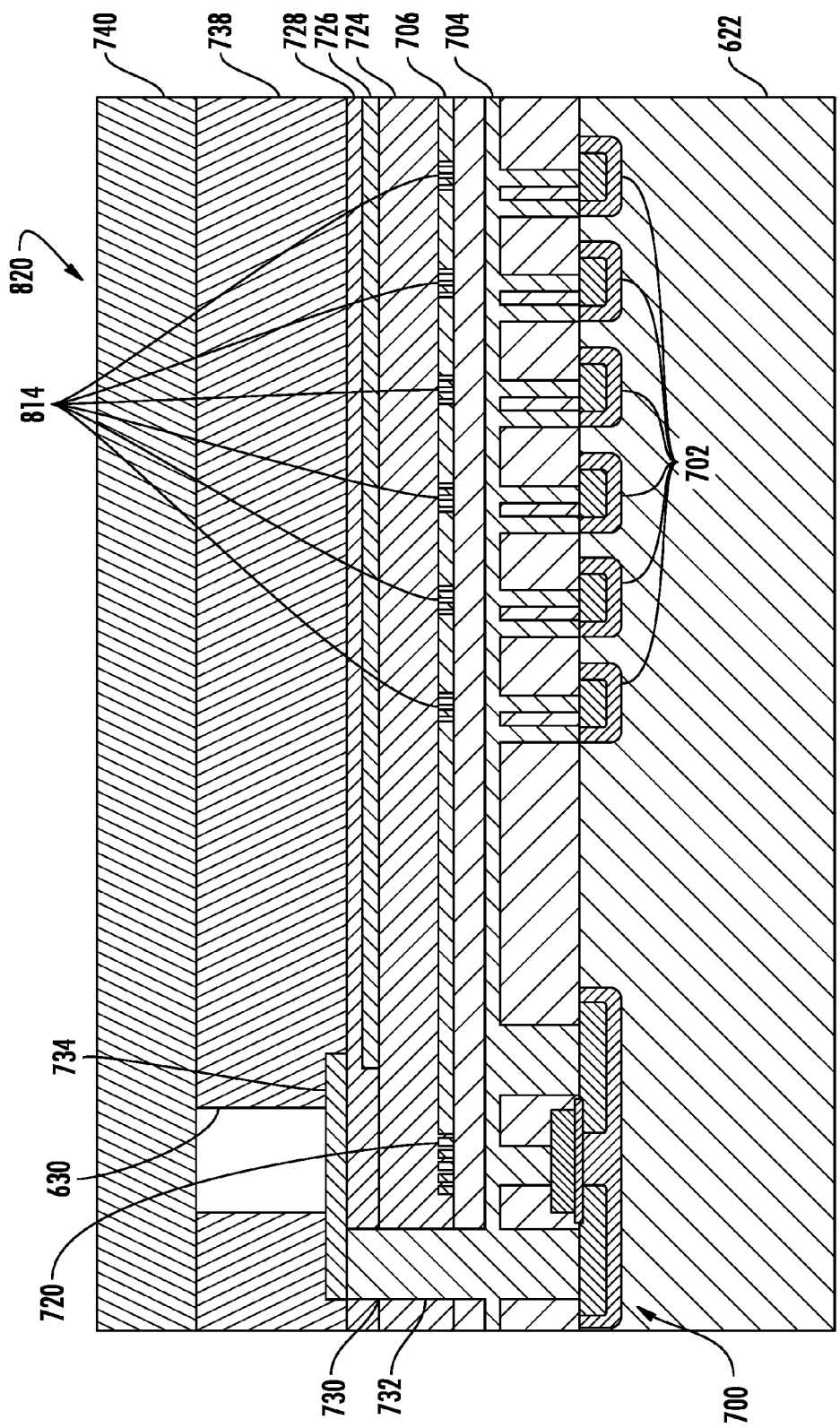
FIG. 19 is a sectional view schematically illustrating another example microfluidic fluid sensor.
Figure 20:
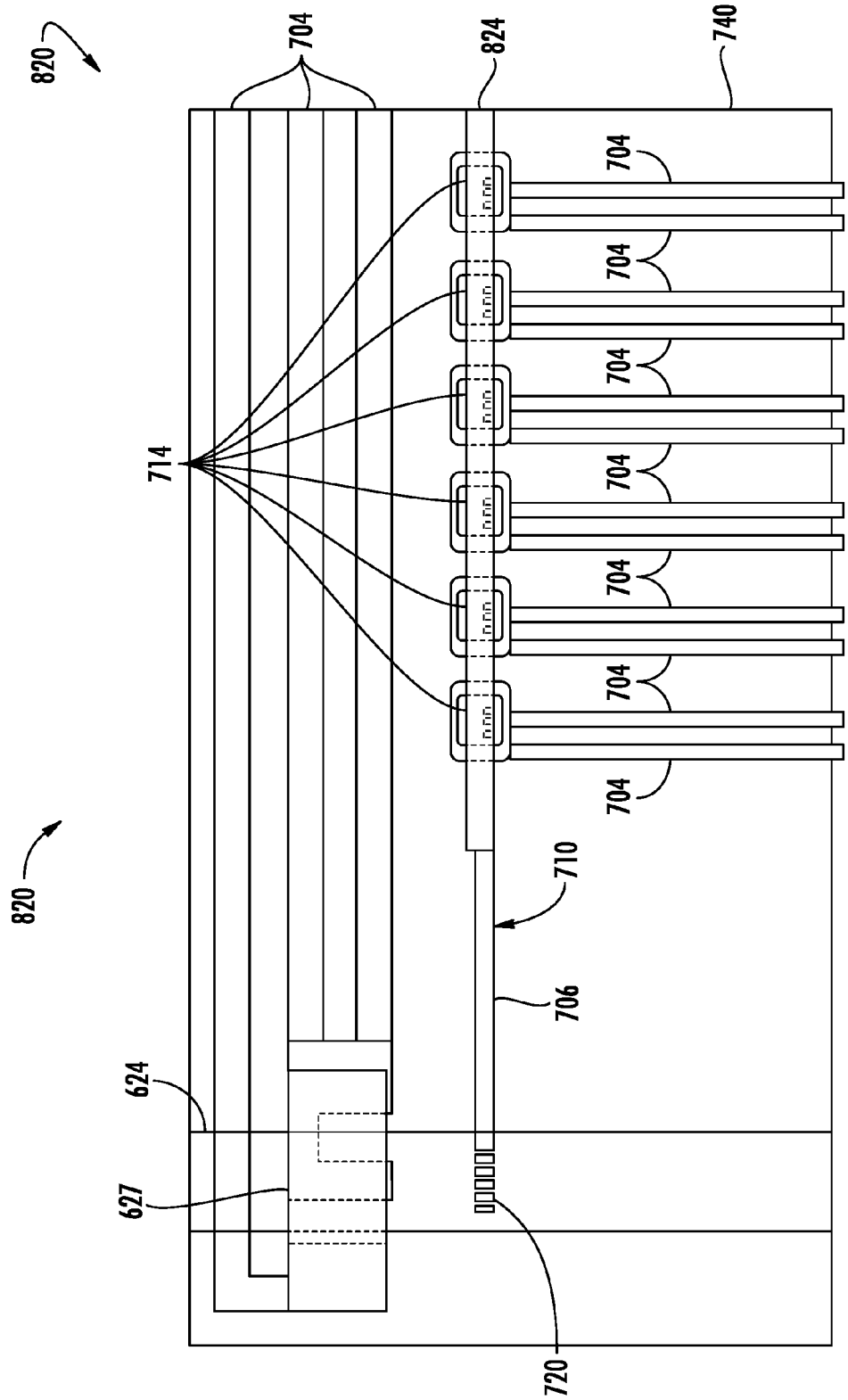
FIG. 20 is a top view of the microfluidic fluid sensor of FIG. 19.

FIGS. 19 and 20 illustrate microfluidic fluid sensor 820, another implementation of microfluidic sensor 20. Microfluidic fluid sensor 820 is similar to microfluidic fluid sensor 620 except that sensor 820 comprises waveguide layer 824 in lieu of waveguide layer 724. Waveguide layer 824 is itself similar to waveguide layer 724, except that waveguide layer 824 has an orientation 90° offset from that of waveguide layer 724. In other words, waveguide layer 824 is oriented horizontally such that the waveguide layer 824 has gratings 814 reference serving as output couplers) which face and horizontal directions rather than the vertical directions of gratings 714. One advantage of this structure is that in one implementation the structure may be fabricated with a single photolithography step, rather than with three steps. Those remaining components of microfluidic fluid sensor 820 which otherwise correspond to components of microfluidic fluid sensor 620 are numbered similarly.

In the examples illustrated in FIGS. 1-20, the waveguide layer 706, waveguide 127 or waveguides 327 are formed upon substrate 22 over top of the previously formed optical sensors 28, 328, 702. In one implementation, waveguide layer 706, waveguide 127 or waveguides 327 are formed using integrated circuit complementary metal-oxide semiconductor (CMOS) thermal inkjet fabrication processes. During such fabrication processes, output couplers 38 or gratings 714, 814 are fabricated in alignment with the optical sensors 28, 328, 702 with a photomask process. As a result, assembly complexity may be reduced.

Figure 21:
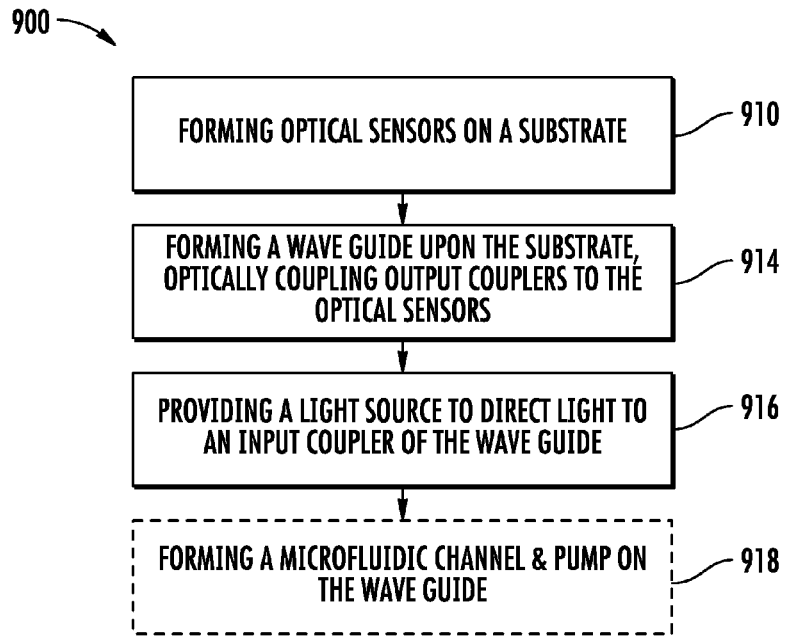
FIG. 21 is a flow diagram of an example method for forming spectrometer and a microfluidic fluid sensor including the spectrometer.

FIG. 21 is a flow diagram of an example method 900 for forming the spectrometer which is a part of each of the above described microfluidic fluid sensors. As indicated by block 910, optical sensors 28, 328 or 702 are formed upon substrate 22. In one implementation, such optical sensors are formed using CMOS fabrication processes. As indicated by block 914, waveguide layer 706 which provides input couplers 36, 720 and output couplers 38 or gratings 714, 814 is deposited upon substrate 22. Through a photomask process, the output couplers 38 or gratings 714, 814 are precisely aligned with the optical sensors 28, 328 or 702, respectively. As indicated by block 916, a light source is provided or formed to direct light to the input coupler 36, 720. In one implementation, the light source is provided by forming a transparent cover a glass. In one implementation, light source additionally comprise a lens. In some implementations, the light source comprises a light emitter, such as a light emitting diode.

As indicated by block 918, in applications where the thus formed spectrometer is to be used as part of a microfluidic fluid sensor, such as those described above, a microfluidic channel and a pump are formed over or above the waveguide. Thus, each of the components is formed through layer by layer CMOS fabrication processes, reducing any assembly for either the spectrometer or the microfluidic fluid sensor that utilizes the spectrometer.

FIG. 21 is a sectional view illustrating an example spectrometer 1020 formed by blocks 910, 914 and 916 of method 900. Spectrometer 1020 comprises substrate 22, waveguide layer 706, reflective layer 1021 and optical sensors 628. Substrate 22 and waveguide layer 706 are as described above. Reflective layer 1021 serves as a mirror, retaining light within waveguide layer 706.

As shown by FIG. 21, optical sensors 28 are formed directly upon substrate 22. Waveguide layer 706 is formed on top of optical sensors 28. Reflective layer 1021 is formed on top of waveguide layer 706. Thus, spectrometer 1020 may be formed with a stack of layers. In the example illustrated, reflective layer 1021 does not extend over input coupler 720, allowing an external light source 1030 supply light to input coupler 720. As indicated by broken lines, in other implementations, reflective layer 1021 may extend over and across input coupler 720, wherein portions of substrate 22 beneath input coupler 720 (as indicated by reference numeral 1023) may be removed to form a light passage or may be made transparent. In such an implementation, an underlying light source 1030' may direct light to input coupler 720.

Figure 22:
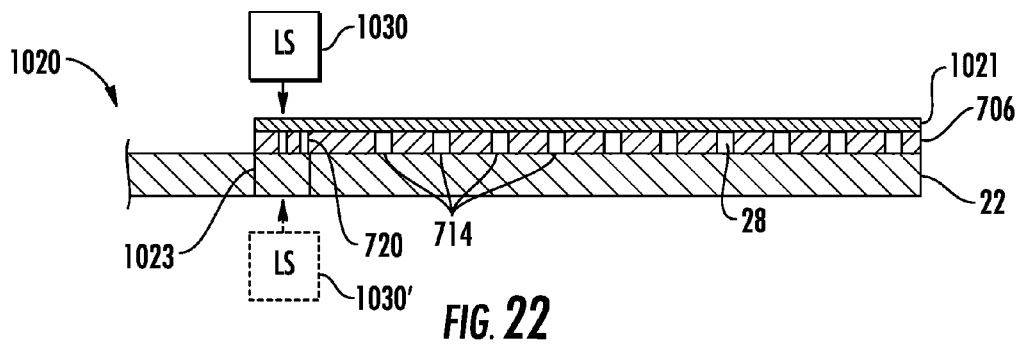
FIG. 22 is a sectional view of an example spectrometer.
Figure 23:
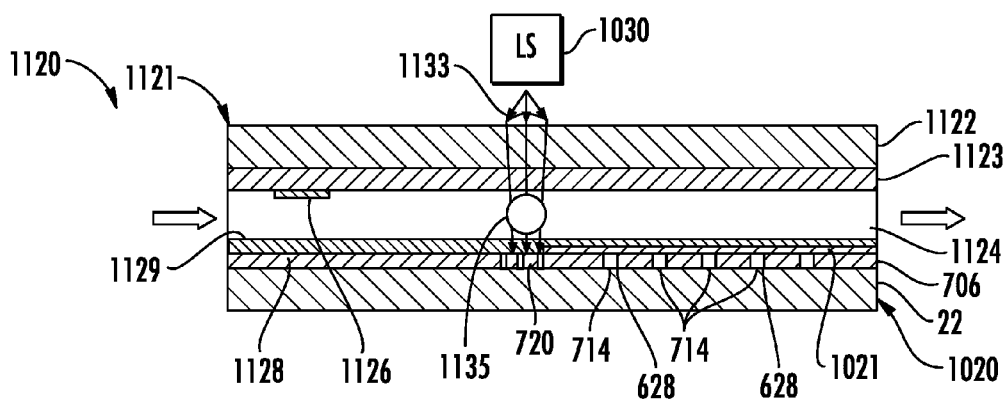
FIG. 23 is a sectional view of a microfluidic fluid sensor formed with the spectrometer of FIG. 21.

FIG. 22 illustrates the use of spectrometer 1020, formed as a single chip, in FIG. 21 to form a microfluidic fluid sensor 1120. As shown by FIG. 22, microfluidic fluid sensor 1120 is formed by bonding a second chip 1121 to the spectrometer 1020. The second chip 1121 comprises substrate 1122, electrical interconnect layer 1123, microfluidic channel 1124, microfluidic pump 1126 and bonding layers 1128, 1129. Substrate 1122 comprises a substrate supporting electrical interconnect layer 1123 and microfluidic pump 1126. In one implementation, substrate 1122 is substantially similar to substrate 22.

Electrical interconnect layer 1123 may comprise a dielectric layer in which are patterned electrically conductive traces or wires as well as a transistor for selectively actuating microfluidic pump 1126. In one implementation, electrical interconnect layer 1123 is similar to layer 623, transistor 701 interconnect 704 described above. As shown by FIG. 22, portions of substrate 1122 and electrical interconnect layer 1123 have openings and/or are transparent to facilitate transmission of light from a light source 1030 through substrate 1122 and layer 1123 and into microfluidic channel 1124. In the example illustrated, chip 1121 comprises an optional lens 1133 to focus light from light source 1030 upon input coupler 720 when chip 1121 is joined to the chip providing spectrometer 1020. As shown by FIG. 22, such light is incident upon cells or other particles 1135 (schematically represented) be carried within the fluid within microfluidic channel 1124.

Microfluidic channel 1124 comprises a passage sized and shaped to extend opposite to input coupler 720 of waveguide layer 706. Microfluidic channel 1124 directs fluid pumped by microfluidic pump 1126 between light from light source 1030 and input coupler 720. Microfluidic pump 1126 is similar to microfluidic pump 734 described above. In the example illustrated, microfluidic pump 1126 comprises a bubble jet inertial pump. In other implementations, microfluidic pump 1126 may comprise other forms of pumps, such as a piezo resistive inertial pump.

Bonding layers 1128, 1129 facilitate securement of chip 1121 to spectrometer 1022 form a two chip microfluidic spectrometer or microfluidic fluid sensor 1120. In one implementation, bonding layer 1128 comprises tetraethyl orthosilicate (TEOS). Bonding layer 1129 comprise an adhesive or primer. In other implementations, bonding layers 1128 and/or 1129 may comprise other adhesives or other bonding materials. Because optical sensors 628 and out couplers 714 of waveguide 706 are formed upon a single chip for single substrate, alignment of optical sensors 628 and out couplers 714 may be achieved, thereby facilitating greater tolerances for the assembly of chip 1121 to the chip forming spectrometer 1020.

Although the present disclosure has been described with reference to example implementations, workers skilled in the art will recognize that changes may be made in form and detail without departing from the spirit and scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. An apparatus comprising:
   a microfluid sensor to detect characteristics of a fluid, the microfluid sensor including a substrate;
   a light source supported by the substrate to direct light to an input coupler of a waveguide;
   a microfluidic channel supported by the substrate to direct the fluid, the microfluidic channel comprising:
      an optical spectrometer integrated with the microfluidic channel as a part of a chip;
      the waveguide supported by the substrate, the waveguide comprising the input coupler and outcouplers; and
      optical sensors supported by the substrate, each of the optical sensors optically coupled to one of the outcouplers; and
   a reference microfluidic channel supported by the substrate, the reference microfluidic channel comprising a fluid input having a pillar filter to provide a reference fluid, wherein the reference fluid is compared to the fluid directed by the microfluidic channel to determine the characteristics of the fluid.

2. The apparatus of claim 1 further comprising a microfluidic pump supported by the substrate to move fluid through the microfluidic channel.

3. The apparatus of claim 2, wherein the microfluidic pump comprises a thermal inkjet resistor.

4. The apparatus of claim 1, wherein the optical sensors and the outcouplers are on a same side of the microfluidic channel.

5. The apparatus of claim 1, wherein the optical sensors and the outcouplers are on opposite sides of the microfluidic channel.

6. The apparatus of claim 1 further comprising:
   a second microfluidic channel supported by the substrate;
   a second waveguide supported by the substrate, the waveguide comprising a second input coupler and second outcouplers; and
   a second light source to direct a second light, different than the light, across the second microfluidic channel into engagement with the second input coupler of the second waveguide; and
   second optical sensors supported by the substrate, each of the second optical sensors optically coupled to one of the second outcouplers.

7. The apparatus of claim 1, wherein the reference microfluidic channel further comprises:
   a reference waveguide supported by the substrate, the reference waveguide comprising a reference coupler and reference outcouplers; and
   reference optical sensors supported by the substrate, each of the optical sensors optically coupled to one of the reference outcouplers.

8. The apparatus of claim 1, wherein the light source is located to direct light across the microfluidic channel to the input coupler of the waveguide.

9. The apparatus of claim 1, wherein the outcouplers are located to direct selected wavelengths of light across the microfluidic channel towards their respective optical sensors.

10. An apparatus comprising:
a microfluid sensor to detect characteristics of a fluid, the microfluid sensor including a substrate;
a light source supported by the substrate to direct light at a coupler of a waveguide;
a microfluidic channel supported by the substrate to direct the fluid, the microfluidic channel comprising:
an optical spectrometer integrated with the microfluidic channel as a part of a chip;
optical sensors supported by the substrate; and
the waveguide formed on the optical sensors, the waveguide including the coupler and outcouplers, each of the outcouplers are operably coupled to one of the optical sensors; and
a reference microfluidic channel supported by the substrate, the reference microfluidic channel comprising a fluid input having a pillar filter to provide a reference fluid, wherein the reference fluid characteristics are compared to the characteristics of the fluid directed by the microfluidic channel.

11. The apparatus of claim 10 wherein the microfluidic channel is between the light source and the coupler of the waveguide.

12. The apparatus of claim 10 further comprising a microfluidic pump supported by the substrate, wherein the microfluidic pump, the optical sensors and the outcouplers are on a same side of the microfluidic channel.

13. A method comprising:
forming optical sensors on a substrate;
forming a microfluidic channel on the substrate to direct a fluid;
forming an optical spectrometer integrated with the microfluidic channel as a part of a chip;
forming a waveguide on the substrate, the waveguide having a coupler and outcouplers, wherein the outcouplers are optically coupled to the optical sensors during their formation using a photo-mask process;
providing a light source to direct light to the coupler of the waveguide; and
forming a reference microfluidic channel supported on the substrate, the reference microfluidic channel comprising providing a reference fluid to a fluid input having a pillar filter, wherein the reference fluid characteristics are compared to the characteristics of the fluid directed by the microfluidic channel.

14. The method of claim 13 further comprising forming a fluid sensor integrated upon the chip including the microfluidic channel on the waveguide.

15. The method of claim 13 further comprising forming a microfluidic pump on the substrate.

* * * * *